(12) United States Patent
Townshend et al.

(10) Patent No.: US 8,242,092 B2
(45) Date of Patent: Aug. 14, 2012

(54) PROTEIN TYROSINE PHOSPHATASE INHIBITORS

(76) Inventors: Brent Townshend, Menlo Park, CA (US); Michel Tremblay, Montreal (CA)

( * ) Notice: Subject to any disclaimer, the term of this patent is extended or adjusted under 35 U.S.C. 154(b) by 32 days.

(21) Appl. No.: 12/366,562

(22) Filed: Feb. 5, 2009

(65) Prior Publication Data
US 2009/0275637 A1  Nov. 5, 2009

Related U.S. Application Data

(60) Provisional application No. 61/063,774, filed on Feb. 5, 2008.

(51) Int. Cl.
*A61K 48/00* (2006.01)

(52) U.S. Cl. ...... 514/44; 536/24.5; 536/536; 536/24.31; 536/24.1

(58) Field of Classification Search .......... None
See application file for complete search history.

(56) References Cited

U.S. PATENT DOCUMENTS

| | | | | |
|---|---|---|---|---|
| 5,580,737 A | * | 12/1996 | Polisky et al. | ..................... 435/6 |
| 6,927,024 B2 | | 8/2005 | Dodge et al. | |

FOREIGN PATENT DOCUMENTS

| | | |
|---|---|---|
| WO | WO 01/96559 A2 | 12/2001 |
| WO | WO 01/96559 A3 | 7/2003 |
| WO | WO 03/070881 A2 | 8/2003 |
| WO | WO 03/070881 A3 | 7/2004 |
| WO | WO 2004/071407 A2 | 8/2004 |
| WO | WO 2004/071407 A3 | 1/2006 |
| WO | WO 2007/028145 A2 | 3/2007 |
| WO | WO 2007/028145 A3 | 10/2007 |

OTHER PUBLICATIONS

Bourdeau et al. Cytoplasmic protein typrosine phosphatases, regulation and function: the roles of PTP1B and TC-PTP. Current Opinion in Cell Biology 2005, vol. 17:203-209.*
Yan et al. Frontiers in Bioscience 10, 1802-1827, 2005.*
Bell et al. Journal of Biological Chemistry; vol. 272:14309-14314, 1998.*
International Search Report dated Oct. 8, 2009 for PCT/US2009/033276.
Xu, et al. Reduction of PTP1B by RNAi upregulates the activity of insulin controlled fatty acid synthase promoter. Biochem Biophys Res Commun. Apr. 8, 2005;329(2):538-43.
Julien, et al. Protein tyrosine phosphatase 1B deficiency or inhibition delays ErbB2-induced mammary tumorigenesis and protects from lung metastasis. Nat Genet. Mar. 2007;39(3):338-46.
Lee, et al. Recent development of small molecular specific inhibitor of protein tyrosine phosphatase 1B. Med Res Rev. Jul. 2007;27(4):553-73.
Montalibet, et al. Residues distant from the active site influence protein-tyrosine phosphatase 1B inhibitor binding. J Biol Chem. Feb. 24, 2006 ;281(8):5258-66.
Shen, et al. Acquisition of a specific and potent PTP1B inhibitor from a novel combinatorial library and screening procedure. J Biol Chem. Dec. 14, 2001;276(50):47311-9.
Stuible, et al. PTP1B and TC-PTP: regulators of transformation and tumorigenesis. Cancer Metastasis Rev. Jun. 2008;27(2):215-30.
Zhang, et al. PTP1B as a drug target: recent developments in PTP1B inhibitor discovery. Drug Discov Today. May 2007;12(9-10):373-81.

* cited by examiner

*Primary Examiner* — Kimberly Chong
(74) *Attorney, Agent, or Firm* — Wilson Sonsini Goodrich & Rosati

(57) ABSTRACT

The present invention provides compositions and methods for binding and/or modulating enzymatic activity of human protein tyrosine phosphatases such as PTP1B. Additionally, the invention provides methods of identifying and using such nucleic acid ligands.

9 Claims, 13 Drawing Sheets

Figure 11

PROTEIN TYROSINE PHOSPHATASE INHIBITORS

CROSS-REFERENCE

This application claims the benefit of U.S. Provisional Application No. 61/063,774 filed on Feb. 5, 2008, which application is incorporated herein by reference.

BACKGROUND OF THE INVENTION

Protein tyrosine phosphatases (PTP) play a critical role in transduction in numerous signal pathways, regulation of cellular functions and immune response. Of the family of PTP's, PTP1B has emerged as a particularly interesting possible target because it is overexpressed in several human diseases. As an intracellular PTP, it is implicated in the regulation of insulin sensitivity through dephosphorylation of the insulin receptor (Elchebly et al, (1999) Science 283(5407), 1544-1548, Klaman et al (2000) Molecular and Cellular Biology 20(15), 5479-5489). PTP1B$^{-/-}$ knockout mice exhibit lower blood glucose and lower insulin concentrations after feeding as well as greater sensitivity to insulin injections. These results suggest that PTP1B is a therapeutic target for type 2 diabetes. A recent report of early phase II clinical trials by Isis Pharmaceuticals using PTP1B mRNA-targeted antisense oligonucleotides indicates that targeting PTP1B proteins can be therapeutically beneficial in type 2 diabetic patients (Havel et al (2007), American Diabetes Association 67th Scientific Sessions, Chicago, Ill.). Additionally, PTP1B-deficient mice are also resistant to weight gain under conditions that would normally lead to obesity, likely due to dephosphorylation of JAK2 by PTP1B resulting in increased leptin sensitivity (Zabolotny et al (2002) Developmental cell 2(4), 489-495; Bence et al (2006) Nature medicine 12(8), 917-924; Cheng et al (2002) Developmental cell 2(4), 497-503). Furthermore, it has been recently shown that deletion of PTP1B activity in transgenic mice bred to develop mammary tumors results in significant increases in tumor latency and resistance to lung metastasis (Julien, S. G. et al (2007) Nature genetics 39(3), 338-346).

Although some progress has been made in the study of the structure, catalytic mechanism, regulation, and localization of the general class of protein tyrosine phosphatases, the inhibitors of PTP1B that have been discovered so far have shown significant limitations. For example, there has been very limited success to date in achieving high selectivity with respect to T-cell phosphatase (TC-PTP), which is nearly identical to PTP1B. Thus, there remains a need for potent and selective PTP inhibitors in general and PTP1B inhibitors specifically.

SUMMARY OF THE INVENTION

The present invention addresses this and other needs by providing nucleic acid ligands which show binding affinity and/or ability to modulate the enzymatic activity of protein tyrosine phosphatases.

The present invention provides a non-naturally occurring nucleic acid ligand which exhibits binding specificity to human protein tyrosine phosphatases. In some embodiments, the human protein tyrosine phosphatase is PTP1B. In other embodiments, the binding specificity is characterized by a $K_d$ of less than about 0.5, 1, 5, 10, 20, 50, 150 or 200 nM. In still other embodiments, the nucleic acid ligand further exhibits inhibition of an enzymatic activity of PTP1B, such as phosphatase activity. In exemplary embodiments, the inhibition is characterized by a $K_i$ of less than 0.5, 1, 5, 10, 15, 20, 25, 50, 75 or 100 nM.

The nucleic acid ligand of the invention may comprise a ribonucleic acid sequence. In some embodiments, the length of the nucleic acid ligand is from about 10 to about 300 nucleotides, from about 15 to about 300 nucleotides, from about 10 to about 300 or from about 10 to about 100 nucleotides.

The invention also provides a modulator of human protein tyrosine phosphatase 1B (PTP1B). In some embodiments, the invention provides an inhibitor of human PTP1B, wherein the inhibitor reduces a phosphatase activity of PTP1B more strongly than a phosphatase activity of T-cell protein tyrosine phosphatase (TC-PTP). In some embodiments, the inhibitor reduces a phosphatase activity of PTP1B at least about 10, 20, 30, 50, 75, 100, 200 or 300 times more strongly than a phosphatase activity of TC-PTP. In other embodiments, the inhibitor reduces a phosphatase activity of PTP1B about 10, 20, 30, 50, 75, 100, 200 or 300 times more strongly than a phosphatase activity of TC-PTP. For example, an inhibitor of the invention reduces a phosphatase activity of PTP1B at least 10 or 100 times more strongly than a phosphatase activity of TC-PTP and the inhibitor is characterized by a $K_i$ of less than 20 or 100 nM.

The scope of the invention also encompasses complexes of a non-naturally occurring nucleic acid ligand and a human protein tyrosine phosphatase. In some embodiments, the complex comprises PTP1B protein. In other embodiments, the complex comprises a ribonucleic acid sequence.

In still other embodiments, the invention provides a collection of polynucleotides comprising a plurality of nucleic acids of which at least one nucleic acid molecule comprises a ribonucleic acid sequence and exhibits binding specificity to a human protein tyrosine phosphatase. At least one nucleic acid may exhibit inhibition of an enzymatic activity of a human protein tyrosine phosphatase, such as phosphatase activity. In some embodiments, at least about 5% of the nucleic acids in the collection exhibit binding specificity to a human protein tyrosine phosphatase. In other embodiments, the collection comprises at least about 10, $10^2$, $10^3$, $10^5$, $10^8$, $10^{10}$ or $10^{12}$ distinct nucleic acid sequences. In yet other embodiments, the human protein tyrosine phosphatase is PTP1B. In some embodiments, the collection may be partially or entirely immobilized on a solid support.

The invention also provides a method for reducing an enzymatic activity of a human protein tyrosine phosphatase comprising contacting said human protein tyrosine phosphatase with an effective amount of nucleic acid ligand of claim 1. In some embodiments, the human protein tyrosine phosphatase is PTP1B. In other embodiments, the nucleic acid ligand comprises a ribonucleic acid. In still other embodiments, the nucleic acid ligand inhibits the activity of PTP1B about 10, 50, or 100 times more strongly than the activity of TC-PTP. In still other embodiments of this method, the nucleic acid ligand comprises a sequence as shown in Table 3.

Included in the invention are also polynucleotides comprising a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

In another embodiment, the invention relates to a method of inhibiting the activity of protein tyrosine phosphatase 1B (PTP1B) expressed in vivo in a cell comprising introducing to the cell a vector encoding a sequence comprising a nucleic acid ligand of the invention.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 11 shows the nucleic acid sequence of the PTP1B gene.

DETAILED DESCRIPTION OF THE INVENTION

Figure 1:
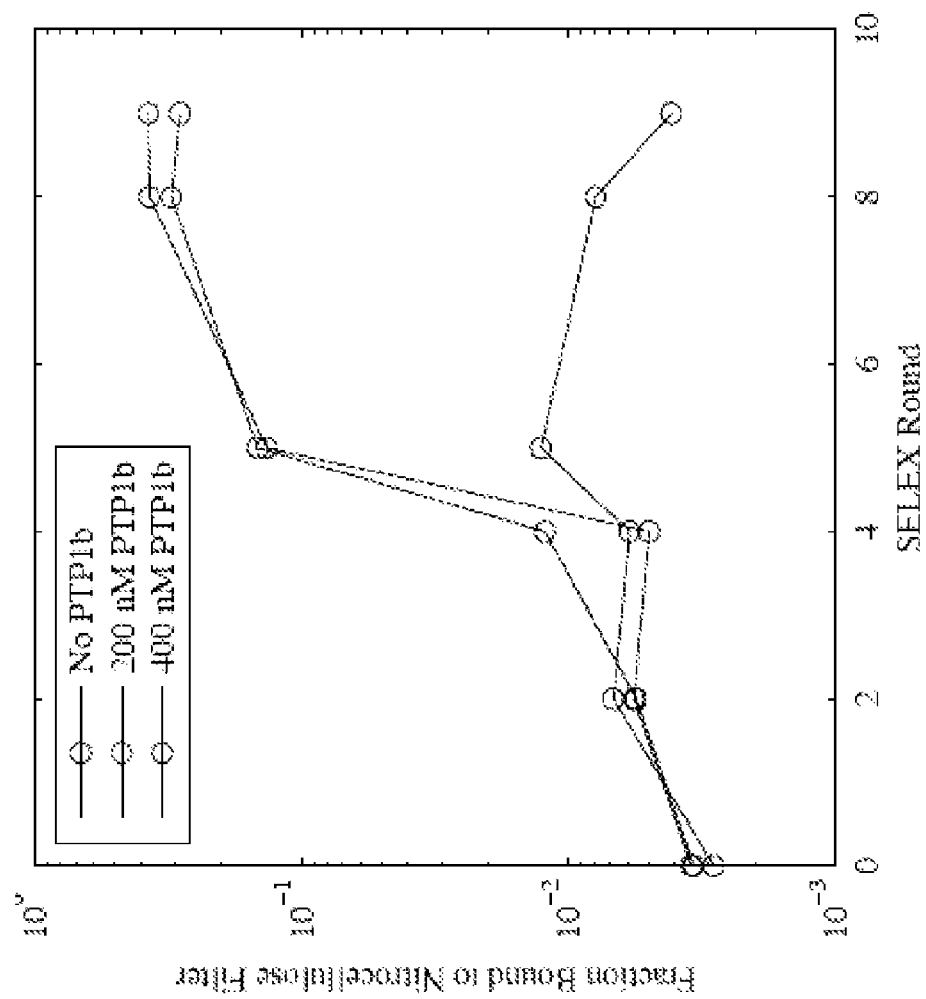
FIG. 1 illustrates filter retention as a function of SELEX round number. DNA from each round was transcribed with a radiolabel and then filtered using the same method as during the selection rounds, with 0, 200, and 400 nM of PTP1B. Radioactivity of the filter and the flow-through was then counted and the above ratios were found.

This invention provides novel modulators of human protein tyrosine phosphatases which are nucleic acid ligands. For example, the modulators of the invention may be inhibitors. The nucleic acid ligands of the invention may exhibit high binding affinity to their target, or they may exhibit high specificity to their target, such as PTP1B protein, relative to other closely related proteins such as TC-PTP. This and other aspects of the invention will be described in further detail below.

Definitions

The terms "polynucleotide", "nucleic acid", "nucleotide" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, nucleic acid ligands (aptamers), isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

A "nucleic acid ligand" is a nucleic acid which exhibits specific interactions such as binding specificity, activation or inhibition of enzymatic activity with a target molecule. Nucleic acid ligands encompass sequences which comprise additional modifications or nucleic acid sequences which confer desirable properties, such as stability (including more stable folding), nuclease resistance, enzymatic activity (e.g. when a nucleic acid ligand additionally comprises sequences encoding a ribozyme), or the ability to interact with additional different target molecules.

A "vector" is a nucleic acid molecule, preferably self-replicating, which transfers an inserted nucleic acid molecule into and/or between host cells. The term includes vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions.

A "target" as used in the context of nucleic acid ligands is a biochemical molecule or structure to which the nucleic acid ligand can bind directly or indirectly and where the binding event results in a desired biological function. The target can be a protein ligand or receptor that is inhibited, activated or otherwise acted upon by the nucleic acid ligand. Examples of targets are hormones, cytokines, antibodies or antibody fragments, cell surface receptors, kinases, growth factors and other biochemical structures with biological activity.

The terms "polypeptide", "peptide", "amino acid sequence" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified, for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including but not limited to glycine and both the D or L optical isomers, and amino acid analogs and peptidomimetics. Standard single or three letter codes are used to designate amino acids.

The term "$K_d$" is used to refer to the equilibrium dissociation constant between a particular nucleic acid ligand and a target. Additionally, the term "$K_i$" represents the dissociation constant for inhibitor binding and characterizes the ability of a molecule, such as a nucleic acid ligand, to inhibit the enzymatic activity of a target. Measurement of a $K_i$ value for a ligand/target pair may be performed using a variety of methods known in the art and is exemplified below. A $K_i$ value can be obtained from an $IC_{50}$ value using the Cheng-Prusoff equation (Biochem. Pharmacol. 22:3099-3108, 1973): $K_i=IC_{50}/(1+D/K_d)$, where D is the concentration of a radioligand used in the assay, $K_d$ is the dissociation constant of the radioligand for the target, and $IC_{50}$ is the concentration of competing ligand which displaces 50% of the specific binding of the radioligand. Unless specifically indicated otherwise, $K_i$ values of the nucleic acid ligands of the invention are measured in physiological NaCl conditions.

The term "selectivity" or "specificity" is a measure of the binding or inhibition preferences of a ligand for different targets. The selectivity of a ligand with respect to its target relative to another target is given by the ratio of the respective values of $K_d$ or $K_i$.

"Sequence identity" or "percent sequence identity" with respect to the nucleic acid ligands or polynucleotides identified herein is defined as the percentage of nucleotides in a candidate sequence that are identical with the nucleotides in the nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software.

General Techniques:

The practice of the present invention employs, unless otherwise indicated, conventional techniques of immunology, biochemistry, chemistry, molecular biology, microbiology, cell biology, genomics and recombinant DNA. See Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Design and Preparation of the Nucleic Acid Ligands of the Invention

The nucleic acids of the invention may be identified by SELEX (Systematic Evolution of Ligands by EXponential enrichment), which is a method for the in vitro evolution of nucleic acid molecules with highly specific binding to chosen target molecules. Examples of the use of this method are described in U.S. application Ser. No. 07/536,428, filed on Jun. 11, 1990; U.S. Pat. No. 5,475,096; and U.S. Pat. No. 5,270,163.

The SELEX process is based on the insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. In brief, a step of the SELEX method involves providing a collection of nucleic acids comprising a number of distinct sequences, selecting nucleic acids from the collection based on a desired property such as binding to a target, and amplifying the selected nucleic acids. The amplification step results in the generation of a second collection of nucleic acids which may be subjected to additional cycles of selection and amplification until the nucleic acid sequences remaining in the collection show significant improvement in the desired property. The selection step is often carried out based on the ability of nucleic acids to bind to a biomolecule such as a target protein. For example, starting from a collection of nucleic acids, often comprising a segment of randomized sequence, the mixture is contacted with the target under conditions favorable for binding. Subsequently, unbound nucleic acids are partitioned from those nucleic acids which have bound specifically to target molecules, the nucleic acid-target complexes are dissociated, and the obtained nucleic acids are amplified to yield a ligand-enriched mixture of nucleic acids. The process is then reiterated by repeating the steps of binding, partitioning, dissociating and amplifying through as many cycles as desired to yield highly specific, high affinity nucleic acid ligands to the target molecule.

Nucleic acid ligands obtained by SELEX or undergoing the SELEX process may be tested for desirable properties in a variety of assays. For example, nucleic acid ligands may be tested by performing binding assays to measure the binding between the nucleic acid ligand and its target. For example, filter binding assays may be used where a target protein is immobilized on a nitrocellulose filter. The amount of the bound nucleic acid ligand can be quantitated, allowing a determination of binding affinity. When such a binding assay is performed during SELEX, the bound nucleic acid ligands may be isolated and amplified, and if desired may be subjected to additional rounds of SELEX. Isolated nucleic acid ligands may also be tested for biological activity by determining the ability of the nucleic acid ligands to modulate the activity of a target, such as a protein tyrosine phosphatase. Methods of determining the activity of a protein tyrosine phosphatase are known in the art and include incubation of a sample comprising the target enzyme and the nucleic acid ligand to be tested with a chromogenic or fluorogenic substrate which is hydrolyzed to a detectable form. By comparing the signal obtained in the presence and absence of the nucleic acid ligand a quantitative measure may be obtained of the ability of the nucleic acid ligand to modulate the activity of the enzyme. Such assays for use with phosphatase enzymes include, for example, substrates based on fluorescein diphosphate, DDAO phosphate, ELF 97 phosphate, DiFMUP, 5-Bromo-4-chloro-3-indolyl phosphate, BODIPY FL ATP-γ-S, BODIPY FL GTP-γ-S, and BOLD APB substrates. Such assays as well as others are described in more detail, for example, in the Molecular Probes Handbook (Invitrogen, Carlsbad, Calif.).

A collection of nucleic acids used in SELEX to produce nucleic acid ligands of the invention may generally comprise deoxyribonucleic or ribonucleic acids or mixed ribonucleic/deoxyribonucleic sequences. Various modifications of the SELEX method have been described. For example, U.S. patent application Ser. No. 07/960,093, filed Oct. 14, 1992, now abandoned, and U.S. Pat. No. 5,707,796, describe the use of the SELEX process in conjunction with gel electrophoresis to select nucleic acid molecules with specific structural characteristics, including bent DNA. U.S. patent application Ser. No. 08/123,935, filed Sep. 17, 1993, now abandoned, U.S. Pat. No. 5,763,177 and U.S. Pat. No. 6,011,577, describe a SELEX based method for selecting nucleic acid ligands containing photoreactive groups capable of binding and/or photocrosslinking to and/or photoinactivating a target molecule. U.S. Pat. No. 5,580,737 describes a method for identifying highly specific nucleic acid ligands able to discriminate between closely related molecules, which can be non-peptidic, termed Counter-SELEX. U.S. Pat. No. 5,567,588 describes a SELEX-based method which achieves highly efficient partitioning between oligonucleotides having high and low affinity for a target molecule. The SELEX method also encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985, describing oligonucleotides containing nucleotide derivatives chemically modified at the 5- and 2'-positions of pyrimidines. U.S. Pat. No. 5,580,737 describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," describes oligonucleotides containing various 2'-modified pyrimidines.

The SELEX method also encompasses combining selected oligonucleotides with other selected oligonucleotides and non-oligonucleotide functional units as described in U.S. Pat. No. 5,637,459 and U.S. Pat. No. 5,683,867, describing the combination of the broad array of shapes and other properties, and the efficient amplification and replication properties, of oligonucleotides with the desirable properties of other molecules. The SELEX method further encompasses combining selected nucleic acid ligands with lipophilic compounds or non-immunogenic, high molecular weight compounds in a diagnostic or therapeutic complex as described in U.S. Pat. No. 6,011,020.

One potential problem encountered in the diagnostic use of nucleic acids is that oligonucleotides in their phosphodiester form may be quickly degraded in body fluids by intracellular and extracellular enzymes, such as endonucleases and exonucleases, before the desired effect is manifested. In some embodiments, the nucleic acid ligands of the invention are modified. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases, isocytidine and isoguanidine and the like. Modifications can also include 3' and 5' modifications such as capping. In some embodiments of the instant invention, the nucleic acid ligands are RNA molecules that are 2'-fluoro (2'-F) modified on the sugar moiety of pyrimidine residues. The modifications can be pre- or post-SELEX process modifications. Pre-SELEX process modifications yield nucleic acid ligands with both specificity for their SELEX target and improved in vivo stability. Post-SELEX process modifications made to 2'-OH nucleic acid ligands can result in improved in vivo stability without adversely affecting the binding capacity of the nucleic acid ligand. Other modifications are known to one of ordinary skill in the art. Such modifications may be made post-SELEX process (modification of previously identified unmodified ligands) or by incorporation into the SELEX process. Stability (especially RNase degradation), bioavailability, and cellular delivery are additional considerations in the preparation of therapeutic nucleic acid ligands. RNase sensitivity may be reduced by using 2'-fluoro or 2'-amino modified RNA (Cook, P. D. K., A. M. (1999) 2'-modified oligonucleotides. ISIS Pharmaceuticals, Inc., USA). Other techniques have been developed to improve bioavailability (Healy, J. M. et al (2004) Pharmaceutical research 21(12), 2234-2246).

The nucleic acid ligands of the present invention may be synthesized in solid phase or in solution, more commonly by solid phase synthesis. Detailed descriptions of the procedures for solid phase synthesis of oligonucleotides by phosphite-triester, phosphotriester, and H-phosphonate chemistries are provided, for example, in Itakura, U.S. Pat. No. 4,401,796; Caruthers, et al., U.S. Pat. Nos. 4,458,066 and 4,500,707;

Beaucage, et al., Tetrahedron Lett., 22:1859-1862 (1981); Matteucci, et al., J. Am. Chem. Soc., 103:3185-3191 (1981); Caruthers, et al., Genetic Engineering, 4:1-17 (1982); Jones, chapter 2, Atkinson, et al., chapter 3, and Sproat, et al., chapter 4, in Oligonucleotide Sygmhsis: A Practical Approach, Gait (ed.), IRL Press, Washington D.C. (1984); Froehler, et al., Tetrahedron Lett., 27:469-472 (1986); Froehler, et al., Nucleic Acid Res., 14:5399-5407 (1986); Sinha, et al., Tetrahedron Lett., 24:5843-5846 (1983); and Sinha, et al., Nucl. Acids Res., 12:4539-4557 (1984). For example, the nucleic acid ligands of the invention may be prepared using an automated, solid-phase procedure based on the phosphoramidite approach. In such a method, each nucleotide (including nucleotide analogues) is individually added to the 5'-end of the growing polynucleotide chain, which is attached at the 3'-end to a solid support. The added nucleotides are in the form of trivalent 3'-phosphoramidites that are protected from polymerization by a dimethoxytriyl (or DMT) group at the 5'-position. After base-induced phosphoramidite coupling, mild oxidation to give a pentavalent phosphotriester intermediate, DMT removal provides a new site for polynucleotide elongation. The nucleic acid ligands are then cleaved off the solid support, and the phosphodiester and exocyclic amino groups are deprotected with ammonium hydroxide. These syntheses may be performed on oligo synthesizers such as those commercially available from Perkin Elmer/Applied Biosystems, Inc (Foster City, Calif.), DuPont (Wilmington, Del.) or Milligen (Bedford, Mass.).

The nucleic acid ligands of the invention may also be synthesized by transcription from DNA in vivo. Thus, in another embodiment, the present invention provides a cell comprising a nucleic acid ligand of the invention. In another embodiment of the invention, a DNA construct is provided which encodes a nucleic acid ligand of the invention. The DNA construct may comprise one or more copies of the nucleic acid ligand coupled to a promoter sequence. In related embodiments, the DNA construct may be introduced into a host cell by methods which include, but are not limited to transfection, electroporation, nucleofection or chemical transformation. Once inside the cell, transcription of the construct is initiated such to result in a monomeric or multimeric copy of the nucleic acid of the invention. Similar techniques are described, for example, in U.S. Pat. No. 6,458,559. This category also includes adenovirus-mediated expression systems (Mi, J., Zhang, X., Rabbani, Z. N., Liu, Y., Reddy, S. K., Su, Z., Salahuddin, F. K., Viles, K., Giangrande, P. H., Dewhirst, M. W., Sullenger, B. A., Kontos, C. D., and Clary, B. M. (2007) Mol Ther).

The nucleic acid ligand of the invention can be labeled using any method known in the art, including but not limited to radioactive, light-absorbing, fluorescent, chemiluminescent or other detectable moieties. For example, the nucleic acid sequence may be modified during RNA synthesis by including a conjugation step to a fluorescently labeled phosphoramidite building block. Additional possible modifications by phosphoramidite coupling are known and commercially available from Glen Research, Inc. Alternatively, the nucleic acid ligand incorporating a reacting group such as a nucleophilic group may be reacted postsynthetically with a labeling reagent comprising a group which is reactive with said nucleophilic group. Exemplary labeling reagents which may be used in conjunction with the nucleic acid ligands of the invention include dabsyl, dabcyl, biotin, fluorescein dyes, TAMRA dyes, cyanine dyes (e.g. Cy3, Cy5), rhodamine dyes, pyrene dyes, perylene dyes, coumarin dyes, Black Hole Quencher™ dyes, acridine dyes, DNP dyes, cholesterol, psoralen and EDTA.

Labels may allow visualization or detection of a nucleic acid ligand, e.g., DNA in a cell, following labeling. Preferably, a label (or detectable agent or moiety) is selected such that it generates a signal which can be measured and whose intensity is related (e.g., proportional) to the amount of labeled nucleic acid ligand, e.g., in a sample being analyzed. In array-based detection methods of the invention, the detectable agent is also preferably selected such that it generates a localized signal, thereby allowing spatial resolution of the signal for each spot on the array.

Any of a wide variety of labeling/detectable agents can be used in the practice of the present invention. Suitable detectable agents include, but are not limited to, various ligands, radionuclides (such as, for example, $^{32}P$, $^{35}S$, $^{3}H$, $^{14}C$, $^{125}I$, $^{131}I$, and the like); fluorescent dyes; chemiluminescent agents (such as, for example, acridinium esters, stabilized dioxetanes, and the like); spectrally resolvable inorganic fluorescent semiconductor nanocrystals (i.e., quantum dots), metal nanoparticles (e.g., gold, silver, copper and platinum) or nanoclusters; enzymes (such as, for example, those used in an ELISA, i.e., horseradish peroxidase, beta-galactosidase, luciferase, alkaline phosphatase); colorimetric labels (such as, for example, dyes, colloidal gold, and the like); magnetic labels (such as, for example, Dynabeads™); and biotin, dioxigenin, haptens, and proteins for which antisera or monoclonal antibodies are available.

In certain embodiments, the label comprises a fluorescent moiety. Numerous known fluorescent labeling moieties of a wide variety of chemical structures and physical characteristics are suitable for use in the practice of the present invention. Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine or TMR), coumarin and coumarin dyes (e.g., methoxycoumarin, dialkylaminocoumarin, hydroxycoumarin and aminomethylcoumarin or AMCA), Oregon Green Dyes (e.g., Oregon Green 488, Oregon Green 500, Oregon Green 514), Texas Red, Texas Red-X, Spectrum Red™, Spectrum Green™, cyanine dyes (e.g., Cy-3™, Cy-5™, Cy-3.5™, Cy-5.5™), Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), IRDyes (e.g., IRD40, IRD700, IRD800), and the like. For more examples of suitable fluorescent dyes and methods for coupling fluorescent dyes to other chemical entities see, for example, "The Handbook of Fluorescent Probes and Research Products", 9.sup.th Ed., Molecular Probes, Inc., Eugene, Oreg.

Favorable properties of fluorescent labeling agents to be used in the practice of the invention include high molar absorption coefficient, high fluorescence quantum yield, and photostability. In certain embodiments, labeling fluorophores desirably exhibit absorption and emission wavelengths in the visible (i.e., between 400 and 750 nm) rather than in the ultraviolet range of the spectrum (i.e., lower than 400 nm). Other desirable properties of the fluorescent moiety may include cell permeability and low toxicity, for example if labeling of the nucleic acid polymer is to be performed in a cell or an organism (e.g., a living animal).

Isolation or purification of the nucleic acid ligands of the present invention, where necessary, may be carried out by any of a variety of methods well-known in the art. Purification of nucleic acids is typically performed either by native acrylamide gel electrophoresis, by anion-exchange HPLC as described, for example by J. D. Pearson and F. E. Regnier (J. Chrom., 1983, 255: 137-149) or by reverse phase HPLC (G. D. McFarland and P. N. Borer, Nucleic Acids Res., 1979, 7: 1067-1080). If desired, the sequence of synthetic nucleic acid ligands can be verified using any suitable sequencing method including, but not limited to, chemical degradation (A. M. Maxam and W. Gilbert, Methods of Enzymology, 1980, 65: 499-560), matrix-assisted laser desorption ionization time-of-flight (MALDI-TOF) mass spectrometry (U. Pieles et al., Nucleic Acids Res., 1993, 21: 3191-3196), mass spectrometry following alkaline phosphatase and exonuclease digestions (H. Wu and H. Aboleneen, Anal. Biochem., 2001, 290: 347-352), and the like.

Nucleic acids of the invention may comprise a sequence exhibiting at least 60% sequence identity to any of the sequences shown in Table 3. Alternatively, the polynucleotide comprises a sequence exhibiting at least 70%, 80%, 90% or 95% sequence identity to any of the sequences shown in Table 3. For example, shorter nucleic acid ligands may be synthesized by truncation of the sequence of the nucleic acid ligand designated as C13 in Table 3.

Nucleic acid ligands of the invention may be at least 5, 10, 15, 20, 25, 30, 35, 40, 45, 50, 60, 70, 80 or 90 nucleotides long. In some embodiments, the length of the nucleic acid ligand is from about 10 to about 300 nucleotides, from about 15 to about 300 nucleotides, from about 10 to about 300 or from about 10 to about 100 nucleotides.

The nucleic acid ligands provided herein may exhibit binding specificity to a human protein tyrosine phosphatase such as PTP1B. In some embodiments, the binding specificity as measured by the $K_d$ may be less than about 0.5, 1, 5, 10, 20, 50, 150 or 200 nM. In still other embodiments, the nucleic acid ligand further exhibits inhibition of an enzymatic activity of PTP1B, such as a phosphatase activity. In exemplary embodiments, the inhibition is characterized by a $K_i$ of less than 0.5, 1, 5, 10, 15, 20, 25, 50, 75 or 100 nM. The binding and inhibition properties of a nucleic acid of the invention in relation to any protein tyrosine phosphatase such as PTP1B or TC-PTP may be measured by any methods known in the art. For example, binding may be measured using the radioactive assay described in Example 5 below. Similarly, inhibition of PTP1B may be measured using the DiFMUP assay enabled in Example 7.

The nucleic acids provided by the invention may also act as inhibitors of PTP1B, wherein the inhibitor reduces a phosphatase activity of PTP1B more strongly than a phosphatase activity of TC-PTP. The phosphatase activity may be measured by any assay known in the art, for example by a DiFMUP assay as described herein. The reduction of activity may be measured, for example, as a $K_i$ value. Selectivity may be measured by comparing a reduction of PTP1B activity relative to reduction of TC-PTP activity. In some embodiments, the inhibitor reduces a phosphatase activity of PTP1B at least about 10, 20, 30, 50, 75, 100, 200 or 300 times more strongly than a phosphatase activity of TC-PTP. An inhibitor of the invention may also reduce a phosphatase activity of PTP1B at least 10, 20, 50 or 100 times more strongly than a phosphatase activity of TC-PTP while the inhibitor is characterized by a $K_i$ of less than 10, 20, 50 or 100 nM. In other embodiments, the inhibitor reduces a phosphatase activity of PTP1B about 10, 20, 30, 50, 75, 100, 200 or 300 times more strongly than a phosphatase activity of TC-PTP. In yet other embodiments, the nucleic acid ligand of the invention reduces a phosphatase activity of PTP1B more strongly than the phosphatase activity of a target chosen from the group consisting of Sigma, PEST, LAR, MKPX, PTPN7, SHP-1 or PTPN13. For example, such a nucleic acid may be more than about 10, 20, 30, 50, 75, 100, 200 or 300 times more selective for PTP1B than for a target chosen from the group consisting of Sigma, PEST, LAR, MKPX, PTPN7, SHP-1 or PTPN13.

The scope of the invention also encompasses complexes of a non-naturally occurring nucleic acid ligand and a human protein tyrosine phosphatase. In some embodiments, the complex comprises PTP1B protein. In other embodiments, the complex comprises a ribonucleic acid sequence. The complex may be formed in vivo or in vitro, and may be, for example, pure or in a complex biological mixture or in a cell. The complex may be stable, or may form temporarily. The nucleic acid ligand may also be in equilibrium with its target.

In still other embodiments, the invention provides a collection of polynucleotides comprising a plurality of nucleic acids of which at least one nucleic acid molecule comprises a ribonucleic acid sequence and exhibits binding specificity to a human protein tyrosine phosphatase. At least one nucleic acid may exhibit inhibition of an enzymatic activity of a human protein tyrosine phosphatase, such as phosphatase activity. In some embodiments, at least about 5% of the nucleic acids in the collection exhibit binding specificity to a human protein tyrosine phosphatase. In other embodiments, the collection comprises at least about 10, $10^2$, $10^3$, $10^5$, $10^8$, $10^{10}$ or $10^{12}$ distinct nucleic acid sequences. In yet other embodiments, the human protein tyrosine phosphatase is PTP1B. In some embodiments, the collection may be partially or entirely immobilized on a solid support.

The invention also provides a method for reducing an enzymatic activity of a human protein tyrosine phosphatase comprising contacting said human protein tyrosine phosphatase with an effective amount of nucleic acid ligand of claim 1. In some embodiments, the human protein tyrosine phosphatase is PTP1B. In other embodiments, the nucleic acid ligand comprises a ribonucleic acid. In still other embodiments, the nucleic acid ligand inhibits the activity of PTP1B at least about 10, 50, 100 or 300 times more strongly than the activity of TC-PTP. In still other embodiments of this method, the nucleic acid ligand comprises a sequence as shown in Table 3. In other embodiments, the nucleic acid ligand is administered to a subject in need of treatment for one of the indications disclosed in the application, including diabetes, cancer, and obesity.

Figure 9:
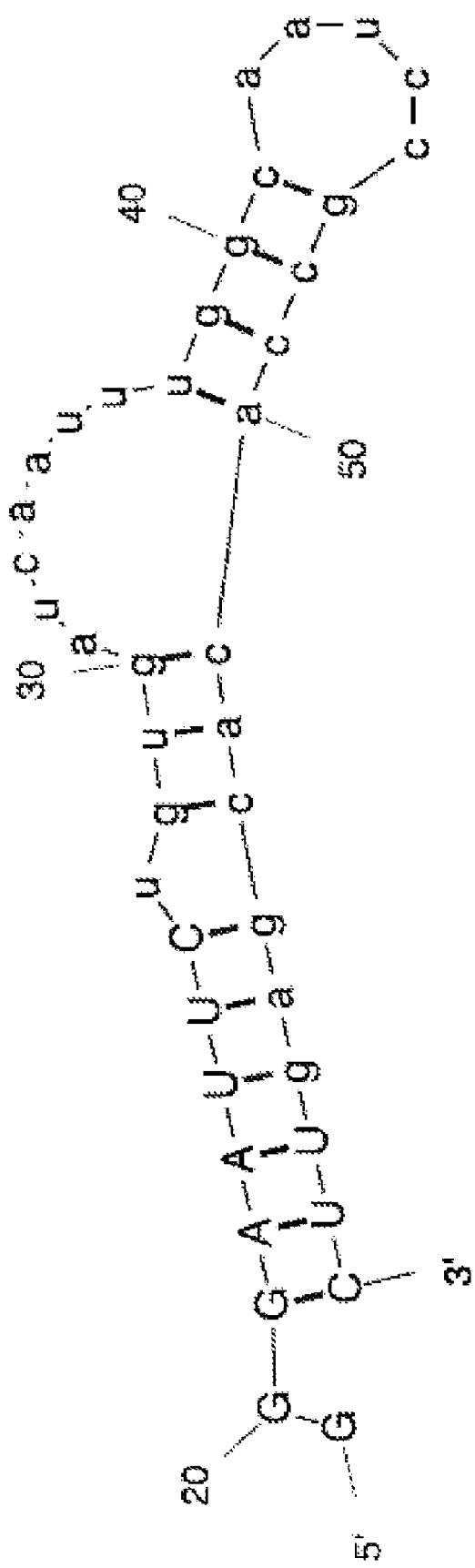
FIG. 9 is an expected secondary structure of the C13M21 nucleic acid ligand. Numbering of nucleotides is based on that used for C13 nucleic acid ligand above. Lower case nucleotides were part of the originally random segment.
Figure 10:
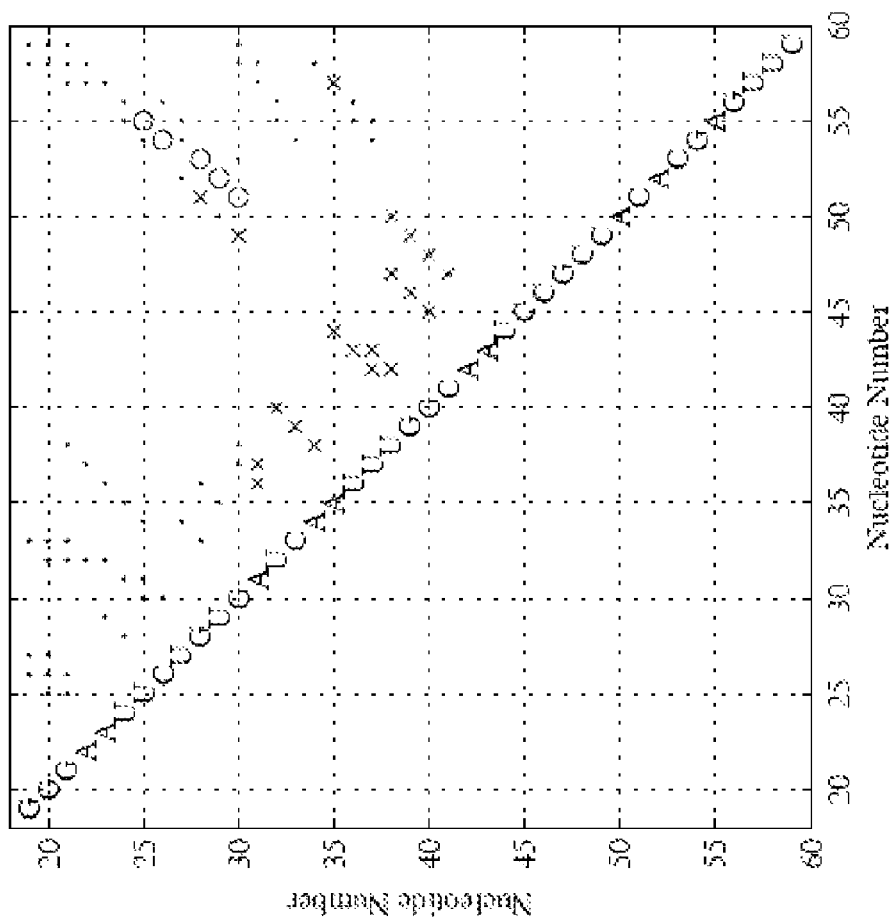
FIG. 10 displays a dot plot of possible base-pairings of C13M21 nucleic acid ligand. Nucleotide numbering is as shown in FIG. 9. The diagonal reproduces the C13M21 sequence. Each point on the plot represents a potential base-pairing of the base shown on the diagonal to the left of the point with the base on the diagonal below the point. "X" marks base-pair swaps that eliminate measurable inhibition, "O" marks base-pair swaps that retain inhibition, dots mark untested base-pairings that were postulated by Unafold.

Included in the invention are also polynucleotides comprising a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3. In some embodiments, the nucleic acid ligand adopts a secondary structure substantially as shown in FIG. 9. As shown in Table 3, it is possible to truncate the sequences identified by SELEX to obtain nucleic acid ligands that maintain binding affinity to a target. Additionally, one skilled in the art may perform mutations or substitutions in the disclosed sequences in order to improve stability or biological properties of the nucleic acid ligand. Such modifications may be made following the guidelines shown in FIG. 10. Additionally, a fraction of the 2'-OH groups in the nucleic acid sequences of the invention may be replaced with 2° F. moieties in order to improve stability.

Target Proteins

In one aspect of the invention, the nucleic acid ligands of the invention may bind proteins such as protein tyrosine phosphatases. Protein tyrosine phosphatases are a class of proteins implicated in a variety of disorders, such as metabolic disorders or cancer. The human genome encodes more than 100 protein tyrosine phosphatases. Of these, a significant fraction are exclusively tyrosine-specific, including phosphatases such as PTP1B and TC-PTP. PTPs display similar catalytic domains but contain diverse non-catalytic motifs and domains; in addition to the inherent substrate specificity of their active sites, the cellular functions of individual PTPs are defined by their subcellular localization and interactions dictated by these other elements.

Figure 13:
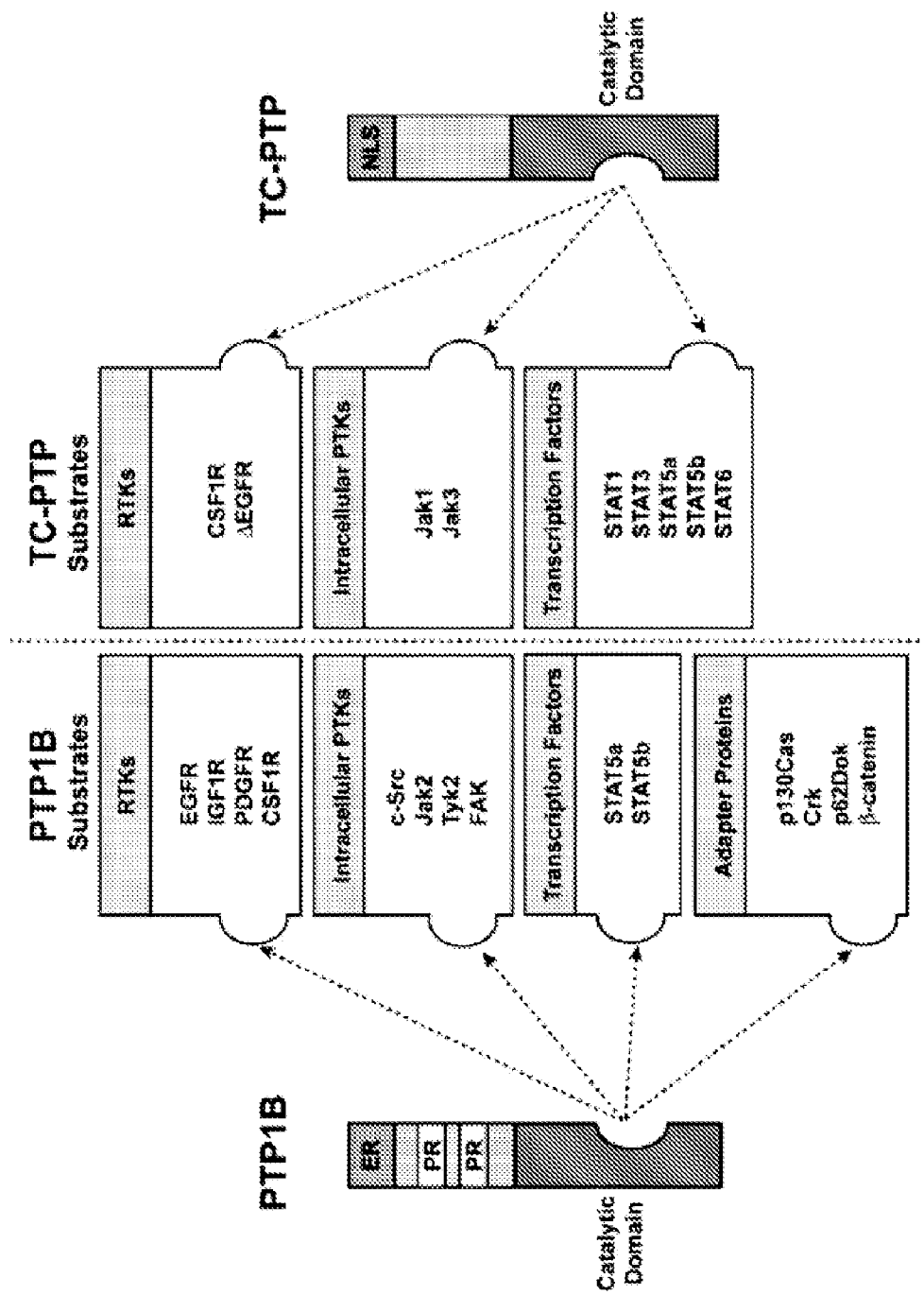
FIG. 13 depicts a schematic representation of the structures of PTP1B and TC-PTP and their respective substrates.

PTP1B consists of an N-terminal catalytic domain, a C-terminal hydrophilic stretch, and an intervening region containing two proline-rich motifs (FIG. 13). The catalytic domain of PTP1B contains a critical cysteine residue within its active site that mediates nucleophilic attack on substrate phosphotyrosine residues. The active site is defined by residues 214 to 221, also designated as the "P-loop", which binds the phosphate group and contains the catalytic Cys residue at position 215. The majority of amino acid residues around the enzymatic active site are conserved in bacterial and mammalian protein tyrosine phosphatases, increasing the importance of secondary binding pockets and peripheral binding sites for the design of selective PTP1B inhibitors. The C-terminus of the protein acts as a tail anchor to localize it to the cytoplasmic face of the ER, likely post-translationally, as a single-stretch transmembrane domain with a short ER-lumenal segment. By contrast, TC-PTP is primarily targeted to the nucleus by a C-terminal nuclear localization sequence (NLS). PTP1B also contains two central proline-rich motifs (PR) which serve as binding sites for proteins including p130Cas, Grb2, and Crk. The structure of the region between the catalytic domain and tail anchor of PTP1B is believed to impair substrate binding and activity of the enzyme. Similarly, C-terminal cleavage of PTP1B is associated with its activation in intact cells. In vivo, PTP1B is regulated by a variety of posttranslational mechanisms, including serine phosphorylation between its catalytic and transmembrane domains, serine phosphorylation within the catalytic domain itself, tyrosine phosphorylation, oxidation due to reactive oxygen species, interaction with SUMO, and spatial separation from its plasma membrane-localized substrates. The nucleic acid ligands of the invention may interact with various structural features of such phosphatases, such as the N-terminal catalytic domain, the C-terminal hydrophilic stretch, and/or the intervening region comprising the proline motifs. For example, the nucleic acid ligand of the invention may bind in the vicinity of the active site located in the N-terminal catalytic domain. However, contacts between the nucleic acid and other residues of the protein located at a distance from the active site may also be present and may contribute to the selectivity of the nucleic acid towards its target. In some embodiments, the binding specificity to the catalytic domain is characterized by a $K_d$ of less than about 0.5, 1, 5, 10, 20, 50, 150 or 200 nM. In other embodiments, the nucleic acid ligand exhibits inhibition of an enzymatic activity of PTP1B, such as phosphatase activity. For example, the inhibition is characterized by a $K_i$ of less than 0.5, 1, 5, 10, 15, 20, 25, 50, 75 or 100 nM. In other embodiments, the nucleic acid ligand comprises a ribonucleic acid. In still other embodiments, the nucleic acid ligand inhibits the activity of PTP1B at least about 10, 50, 100 or 300 times more strongly than the activity of TC-PTP. In still other embodiments of this method, the nucleic acid ligand comprises a sequence as shown in Table 3. Included in the invention are also polynucleotides comprising a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

The role of protein tyrosine phosphatases in metabolic regulation is well characterized. Protein tyrosine phosphatases negatively regulate the pathway of metabolic insulin signal transduction which occurs by activation of the insulin receptor, for example by autophosphorylation of tyrosine residues in the insulin-receptor activation loop, resulting in the recruitment of insulin-receptor substrate proteins and activation of phosphatidylinsositol 3-kinase (PI3K) and downstream protein kinase B (PKB or AKT). Subsequently, glucose transporter GLUT4 is activated. Several protein tyrosine phosphatases, including receptor protein tyrosine phoshpatase-α (rPTP-α), leukocyte antigen-related tyrosine phosphatase (LAR), SH2-domain-containing phosphotyrosine phosphatase (SHP2) and PTP1B are known to modulate insulin signal transduction. PTP1B in particular appears to be a key regulator of insulin-receptor activity that acts on the insulin receptor as well as on other signaling pathway components, including IRS1. By decreasing the activity of protein tyrosine phosphatases such as PTP1B using an inhibitor of the invention, improvements in metabolic regulation of insulin may be observed, such as amelioration of hyperglycaemia and hyperinsulinaemia, and improved insulin and/or leptin sensitivity. In some embodiments, the nucleic acid ligands of the invention increase insulin sensitivity in a subject in need thereof. Such nucleic acids may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

Protein tyrosine phosphatases such as PTP1B and TC-PTP are believed to be involved in the suppression or progression of cellular transformation. PTP1B overexpression partially reverts the transformed phenotype of v-Src-expressing cells, decreases the tumorigenicity of neu-TM-transformed cells in vitro and in vivo, suppresses transformation of Rat-1 cells by BCR-ABL and induces differentiation of BCR-ABL-expressing K562 cells. It is believed that the first proline-rich sequence of PTP1B is involved in mediating suppression of transformation. In some embodiments, the nucleic acid ligands of the invention inhibit the growth of transformed cells. Such nucleic acids may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

PTP1B may also participate in the regulation of integrin signaling and c-Src activation. Cellular adhesion to the extracellular matrix (ECM) is an important factor dictating the migration of individual cells as well as the invasive and metastatic properties of tumors. Integrins, a family of cell-surface transmembrane proteins, play crucial roles in the physical attachment of cells to the ECM as well as in the initiation of signaling at sites of adhesion. Binding of integrins to ECM proteins leads to activation of several PTKs, including FAK and c-Src, resulting in a variety of downstream responses. In many types of human cancer, c-Src activity is elevated. In breast cancer cell lines, this corresponds to an increase in PTP activity capable of activating c-Src by dephosphorylating its inhibitory tyrosine residue (Y530 in human c-Src, Y527 in mouse), an activity which may be attributed to PTP1B. Overall, it is believed that PTP1B is a positive regulator of integrin-mediated pathways. Inhibitors of such pathways may function as anticancer drugs to block both tumor metastasis and angiogenesis. In some embodiments, nucleic acid ligands of the invention inhibit angiogenesis or metastasis. Such nucleic acids may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

PTP1B also plays a role in regulating cell-cell adhesion. The cadherin family of cell-cell adhesion proteins plays crucial roles in development, tissue homeostasis and wound healing. The cadherin extracellular domain mediates homophilic interactions with neighboring cells, while the cytoplasmic domain is linked to the actin cytoskeleton through its association with α-, β- and p120-catenin, as well as actin-regulatory proteins such as vinculin. In various cancers, the loss of E-cadherin, which is normally expressed in epithelial cells, and the associated gain of N-cadherin, which is expressed in a variety of other tissues, is associated with, and may directly cause, increased tumor invasion and metastasis. This transformation likely reflects differences in the strength of the cell-cell contacts formed by N- and E-cadherin, and may be caused by the assembly of distinct cytoplasmic protein complexes and/or altered cadherin avidity. PTP1B associates with the cytoplasmic domain of N-cadherin, promoting the dephosphorylation of β-catenin necessary for formation of the N-cadherin-β-catenin complex. PTP1B may therefore modulate cell-cell adhesion strength, increasing or reducing cell motility and invasion. A nucleic acid of the invention may increase or decrease cell-cell-adhesion strength as determined in an in vitro assay. Such nucleic acids may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

PTP1B has also emerged as a regulator of apoptosis. The dysregulation of programmed cell death is critical to the progression of many types of cancer. A growing number of studies have implicated PTPs in the direct and indirect modulation of apoptotic signaling pathways, and PTP1B has consistently been shown to have a pro-apoptotic function. For example, PTP 1B-null mice are markedly resistant to hepatic failure induced by injection of Jo-2, an agonist of the Fas death receptor, which induces caspase activation and apoptotic cell death. In addition, immortalized PTP1B-null hepatocytes are resistant to serum-withdrawal-induced apoptosis. Thus, PTP1B may play an important role as a negative regulator of RTK signaling. PTP1B may also regulate apoptosis by other mechanisms which include potentiation of ER stress signaling or decrease of pro-survival STAT3 activation by dephosphorylation of JAK2. In this context, a decrease in PTP1B activity may lead to increase in induction of apoptosis. A nucleic acid ligand of the invention may increase the occurrence of apoptosis in a neoplastic cell line. Such nucleic acids may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

Inhibition of protein tyrosine phosphatases may also have utility in disorders involving hematopoiesis and inflammation, by sensitizing leukemic cells to apoptosis by creating an abnormal bone marrow stromal cell environment. Additionally, protein tyrosine phosphatases like TC-PTP and PTP1B act as regulators of macrophage development and activation. Macrophages can play a tumor-supporting role and represent a large population of cells infiltrating stroma. Increased PTP1B protein levels have been documented in patients suffering from chronic myeloid leukemia (CML). PTP1B inhibitors could assist in CML treatment by promoting differentiation of leukemic cells. In some embodiments, a nucleic acid ligand of the invention increases differentiation of leukemic cells. Such nucleic acids may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

Uses of the Nucleic Acid Ligands of the Invention

The nucleic acid ligands of the invention may be used for the treatment of any indication in which it is desirable to modulate (e.g. inhibit) or change the expression (e.g. reduce the expression) of PTP1B. For example, PTP1B has been implicated in diabetes, cancer, and obesity, and in these indications a nucleic acid ligand of the invention may have utility as a treatment. The term "treating" and its grammatical equivalents as used herein includes achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the nucleic acid ligands may be administered to a patient at risk of developing a particular disease, or to a patient reporting one or more of the physiological symptoms of a disease, even though a diagnosis of this disease may not have been made Nucleic acid ligands of the invention may be used, for example, for the treatment of type I diabetes, type II diabetes, impaired glucose tolerance, insulin resistance, obesity, immune dysfunctions including autoimmunity and AIDS, diseases with dysfunctions of the coagulation system, allergic diseases including asthma, osteoporosis, proliferative disorders including cancer and psoriasis, diseases with decreased or increased synthesis or effects of growth hormone, diseases with decreased or increased synthesis of hormones or cytokines that regulate the release of/or response to growth hormone, diseases of the brain including Alzheimer's disease and schizophrenia, and infectious diseases. Such nucleic acids may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

In some embodiments, the nucleic acid ligands of the invention are used to treat, prevent, and/or diagnose cell proliferative disorders such as cancers and neoplastic conditions. Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synoviuma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma. Such nucleic acids may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991), *Crit. Rev. Oncol./Hemotol.* 11:267-97); lymphoid malignancies include, but are not limited to acute lymphoblastic leukemia (ALL) which includes B-lineage ALL and T-lineage ALL, Philadelphia-positive (Ph+) ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Stemberg disease. Nucleic acid ligands of the invention may be used to treat such disorders. Such nucleic acids may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

In one aspect, the invention provides methods of treating breast cancer by administering the nucleic acid ligands of the invention. Breast cancer includes invasive breast carcinomas, such as invasive ductal carcinoma, invasive lobular carcinoma, tubular carcinoma, invasive cribriform carcinoma, medullary carcinoma, mucinous carcinoma and other tumours with abundant mucin, cystadenocarcinoma, columnar cell mucinous carcinoma, signet ring cell carcinoma, neuroendocrine tumours (including solid neuroendocrine carcinoma, atypical carcinoid tumour, small cell/oat cell carcinoma, or large cell neuroendocrine carcioma), invasive papillary carcinoma, invasive micropapillary carcinoma, apocrine carcinoma, metaplastic carcinomas, pure epithelial metaplastic carciomas, mixed epithelia/mesenchymal metaplastic carcinomas, lipid-rich carcinoma, secretory carcinoma, oncocytic carcinoma, adenoid cystic carcinoma, acinic cell carcinoma, glycogen-rich clear cell carcinoma, sebaceous carcinoma, inflammatory carcinoma or bilateral breast carcinoma; mesenchymal tumors such as haemangioma, angiomatosis, haemangiopericytoma, pseudoangiomatous stromal hyperplasia, myofibroblastoma, fibromatosis (aggressive), inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma, or leiomysarcoma; myoepithelial lesions such as myoepitheliosis, adenomyoepithelial adenosis, adenomyoepithelioma, or malignant myoepithelioma; fibroepithelial tumours such as fibroadenoma, phyllodes tumour, low grade periductal stromal sarcoma, or mammary hamartoma; and tumours of the nipple such as nipple adenoma, syringomatous adenoma, or Paget's disease of the nipple. Nucleic acid ligands of the invention may be used to treat such disorders. Such nucleic acids may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

Treatment of breast cancer may be effected in conjunction with any additional therapy, such as a therapy that is part of the standard of care. A surgical technique such as lumpectomy or mastectomy may be performed prior to, during, or following treatment with the nucleic acid ligands of the invention. Alternatively, radiation therapy may be used for the treatment of breast cancer in conjunction with the nucleic acid ligands of the invention. In other cases, the nucleic acid ligands of the invention are administered in combination with a second therapeutic agent. Such an agent may be a chemotherapeutic agent such as an individual drug or combination of drugs and therapies. For example, the chemotherapeutic agent can be an adjuvant chemotherapeutic treatment such as CMF (cyclophosphamide, methotrexate, and 5-fluorouracil); FAC or CAF (5-fluorouracil, doxorubicin, cyclophosphamide); AC or CA (doxorubicin and cyclophosphamide); AC-Taxol (AC followed by paclitaxel); TAC (docetaxel, doxorubicin, and cyclophosphamide); FEC (5-fluorouracil, epirubicin and cyclophosphamide); FECD (FEC followed by docetaxel); TC (docetaxel and cyclophosphamide). In addition to chemotherapy, trastuzumab may also be added to the regimen depending on the tumor characteristics (i.e. HER2/neu status) and risk of relapse. Hormonal therapy may also be appropriate before, during or following chemotherapeutic treatment. For example, tamoxifen may be administered or a compound in the category of aromatase inhibitors including, but not limited to aminogluthetimide, anastrozole, exemestane, formestane, letrozole, or vorozole. In other embodiments, an antiangiogenic agent may be used in combination therapy for the treatment of breast cancer. The antiangiogenic agent may be an anti-VEGF agent including, but not limited to bevacizumab. A nucleic acid ligand of the invention useful for such treatment may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

In another aspect, the nucleic acid ligands of the invention may be used to treat ovarian cancer. Ovarian cancers include ovarian tumors such as, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors. A nucleic acid ligand of the invention useful for such treatment may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

The nucleic acid ligands of the invention may be administered in conjunction with a second therapy such as a therapy that is part of the standard of care. Surgery, immunotherapy, chemotherapy, hormone therapy, radiation therapy, or a combination thereof are some possible treatments available for ovarian cancer. Some possible surgical procedures include debulking, and a unilateral or bilateral oophorectomy and/or a unilateral or bilateral salpigectomy. Anti-cancer drugs that may be used include cyclophosphamide, etoposide, altretamine, and ifosfamide. Hormone therapy with the drug tamoxifen may be used to shrink ovarian tumors. Radiation therapy may be external beam radiation therapy and/or brachytherapy. A nucleic acid ligand of the invention useful for such treatment may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

In another aspect, the nucleic acid ligands of the invention may be used to treat prostate cancer. Prostate cancers include adenocarcinomas and metastasized adenocarcinomas. The nucleic acid ligands of the invention may be administered in conjunction with a second therapy such as a therapy that is part of the standard of care. Treatment for prostate cancer may involve surgery, radiation therapy, High Intensity Focused Ultrasound (HIFU), chemotherapy, cryosurgery, hormonal therapy, or any combination thereof. Surgery may involve prostatectomy, radical perineal prostatectomy, laparoscopic radical prostatectomy, transurethral resection of the prostate or orchiectomy. Radiation therapy may include external beam radiation therapy and/or brachytherapy. Hormonal therapy may include orchiectomy; administration of antiandrogens such as flutamide, bicalutamide, nilutamide, or cyproterone acetate; medications which inhibit the production of adrenal androgens such as DHEA, such as ketoconazole and aminoglutethimide; and GnRH antagonists or agonists such as Abarelix (Plenaxis®), Cetrorelix (Cetrotide®), Ganirelix (Antagon®), leuprolide, goserelin, triptorelin, or buserelin. Treatment with an anti-androgen agent, which blocks androgen activity in the body, is another available therapy. Such agents include flutamide, bicalutamide, and nilutamide. This therapy is typically combined with LHRH analog administration or an orchiectomy, which is termed a combined androgen blockade (CAB). Chemotherapy includes, but is not limited to, administration of docetaxel, for example with a corticosteroid such as prednisone. Anti-cancer drugs such as doxorubicin, estramustine, etoposide, mitoxantrone, vinblastine, paclitaxel, carboplatin may also be administered to slow the growth of prostate cancer, reduce symptoms and improve the quality of life. Additional compounds such as bisphosphonate drugs may also be administered. A nucleic acid ligand of the invention useful for such treatment may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

In another aspect, the nucleic acid ligands of the invention may be used to treat renal cancer. Renal cancers include, but are not limited to, renal cell carcinomas, metastases from extra-renal primary neoplasms, renal lymphomas, squamous cell carcinomas, juxtaglomerular tumors (reninomas), transitional cell carcinomas, angiomyolipomas, oncocytomas and Wilm's tumors. The nucleic acid ligands of the invention may be administered in conjunction with a second therapy such as a therapy that is part of the standard of care. Treatment for renal cancer may involve surgery, percutaneous therapies, radiation therapies, chemotherapy, vaccines, or other medication. Surgical techniques useful for treatment of renal cancer in combination with the nucleic acid ligands of the invention include nephrectomy, which may include removal of the adrenal gland, retroperitoneal lymph nodes, and any other surrounding tissues affected by the invasion of the tumor. Percutaneous therapies include, for example, image-guided therapies which may involve imaging of a tumor followed by its targeted destruction by radiofrequency ablation or cryotherapy. In some cases, other chemotherapeutic or other medications useful in treating renal cancer may be alpha-interferon, interleukin-2, bevacizumab, sorafenib, sunitib, temsirolimus or other kinase inhibitors. A nucleic acid ligand of the invention useful for such treatment may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

In other aspects, the invention provides methods of treating pancreatic cancer by administering nucleic acid ligands of the invention, such as a pancreatic cancer selected from the following: an epitheliod carcinoma in the pancreatic duct tissue and an adenocarcinoma in a pancreatic duct. The most common type of pancreatic cancer is an adenocarcinoma, which occurs in the lining of the pancreatic duct. Possible treatments available for pancreatic cancer include surgery, immunotherapy, radiation therapy, and chemotherapy. Possible surgical treatment options include a distal or total pancreatectomy and a pancreaticoduodenectomy (Whipple procedure). Radiation therapy may be an option for pancreatic cancer patients, specifically external beam radiation where radiation is focused on the tumor by a machine outside the body. Another option is intraoperative electron beam radiation administered during an operation. Chemotherapy may also be used to treat pancreatic cancer patients. Suitable anti-cancer drugs include, but are not limited to, 5-fluorouracil (5-FU), mitomycin, ifosfamide, doxorubicin, streptozocin, chlorozotocin, and combinations thereof. The methods provided by the invention can provide a beneficial effect for pancreatic cancer patients, by administration of a nucleic acid ligand of the invention or a combination of administration of a nucleic acid ligand and surgery, radiation therapy, or chemotherapy. A nucleic acid ligand of the invention useful for such treatment may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

In one aspect, nucleic acid ligands of the invention may be used for the treatment of colon cancer, including but not limited to non-neoplastic polyps, adenomas, familial syndromes, colorectal carcinogenesis, colorectal carcinoma, and carcinoid tumors. Possible treatments available for colon cancer that may be used in conjunction with the nucleic acid ligands of the invention include surgery, chemotherapy, radiation therapy or targeted drug therapy. A nucleic acid ligand of the invention useful for such treatment may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

Radiation therapy may include external beam radiation therapy and/or brachytherapy. Chemotherapy may be used to reduce the likelihood of metastasis developing, shrink tumor size, or slow tumor growth. Chemotherapy is often applied after surgery (adjuvant), before surgery (neo-adjuvant), or as the primary therapy if surgery is not indicated (palliative). For example, exemplary regimens for adjuvant chemotherapy involve the combination of infusional 5-fluorouracil, leucovorin, and oxaliplatin (FOLFOX). First line chemotherapy regimens may involve the combination of infusional 5-fluorouracil, leucovorin, and oxaliplatin (FOLFOX) with a targeted drug such as bevacizumab, cetuximab or panitumumab or infusional 5-fluorouracil, leucovorin, and irinotecan (FOLFIRI) with targeted drug such as bevacizumab, cetuximab or panitumumab. Other chemotherapeutic agents that may be useful in the treatment or prevention of colon cancer in combination with the nucleic acid ligands of the invention are Bortezomib (Velcade®), Oblimersen (Genasense®, G3139), Gefitinib and Erlotinib (Tarceva®) and Topotecan (Hycamtin®). A nucleic acid ligand of the invention useful for such treatment may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

Some embodiments provide methods for the treatment of lung cancer using the nucleic acid ligands of the invention. Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma. A nucleic acid ligand of the invention useful for such treatment may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

The most common type of lung cancer is non-small cell lung cancer (NSCLC), which accounts for approximately 80-85% of lung cancers and is divided into squamous cell carcinomas, adenocarcinomas, and large cell undifferentiated carcinomas. Small cell lung cancer, e.g. small cell lung carcinomas, accounts for 15-20% of lung cancers. Treatment options for lung cancer include surgery, immunotherapy, radiation therapy, chemotherapy, photodynamic therapy, or a combination thereof. Some possible surgical options for treatment of lung cancer are a segmental or wedge resection, a lobectomy, or a pneumonectomy. Radiation therapy may be external beam radiation therapy or brachytherapy. Some anticancer drugs that may be used in chemotherapy to treat lung cancer in combination with the nucleic acid ligands of the invention include cisplatin, carboplatin, paclitaxel, docetaxel, gemcitabine, vinorelbine, irinotecan, etoposide, vinblastine, gefitinib, ifosfamide, methotrexate, or a combination thereof. Photodynamic therapy (PDT) may be used to treat lung cancer patients. The methods described herein can provide a beneficial effect for lung cancer patients, by administration of a nucleic acid ligand or a combination of administration of a nucleic acid ligand and surgery, radiation therapy, chemotherapy, photodynamic therapy, or a combination thereof. A nucleic acid ligand of the invention useful for such treatment may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

Examples of cellular proliferative and/or differentiative disorders of the liver include, but are not limited to, nodular hyperplasias, adenomas, and malignant tumors, including primary carcinoma of the liver and metastatic tumors. A nucleic acid ligand of the invention useful for treatment of such disorders may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

Immunoproliferative disorders (also known as "immunoproliferative diseases" or "immunoproliferative neoplasms") are disorders of the immune system that are characterized by the abnormal proliferation of the primary cells of the immune system, which includes B cells, T cells and Natural Killer (NK) cells, or by the excessive production of immunoglobulins (also known as antibodies). Such disorders include the general categories of lymphoproliferative disorders, hypergammaglobulinemias, and paraproteinemias. Examples of such disorders include, but are not limited to, X-linked lymphoproliferative disorder, autosomal lymphoproliferative disorder, Hyper-IgM syndrome, heavy chain disease, and cryoglobulinemia. Other immunoproliferative disorders can be graft versus host disease (GVHD); psoriasis; immune disorders associated with graft transplantation rejection; T cell lymphoma; T cell acute lymphoblastic leukemia; testicular angiocentric T cell lymphoma; benign lymphocytic angiitis; and autoimmune diseases such as lupus erythematosus, Hashimoto's thyroiditis, primary myxedema, Graves' disease, pernicious anemia, autoimmune atrophic gastritis, Addison's disease, insulin dependent diabetes mellitus, good pasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulceratis colitis, Sjogren's syndrome, rheumatoid arthritis, polymyositis, scleroderma, and mixed connective tissue disease. A nucleic acid ligand of the invention useful for such treatment may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

The invention further provides methods of modulating PTP activity by contacting PTP with an amount of a compound of the invention sufficient to modulate the activity of PTP. Modulation can be inhibition or activation PTP activity. In some embodiments, the invention provides methods of inhibiting PTP activity by contacting PTP with an amount of a compound of the invention sufficient to inhibit the activity of PTP. In some embodiments, the invention provides methods of inhibiting PTP activity in a solution by contacting said solution with an amount of a compound of the invention sufficient to inhibit the activity of PTP in said solution. In some embodiments, the invention provides methods of inhibiting PTP activity in a cell by contacting said cell with an amount of a compound of the invention sufficient to inhibit the activity of PTP in said cell. In some embodiments, the invention provides methods of inhibiting PTP activity in a tissue by contacting said tissue with an amount of a compound of the invention sufficient to inhibit the activity of PTP in said tissue. In some embodiments, the invention provides methods of inhibiting PTP activity in an organism by contacting said organism with an amount of a compound of the invention sufficient to inhibit the activity of PTP in said organism. In some embodiments, the invention provides methods of inhibiting PTP activity in an animal by contacting said animal with an amount of a compound of the invention sufficient to inhibit the activity of PTP in said animal. In some embodiments, the invention provides methods of inhibiting PTP activity in a mammal by contacting said mammal with an amount of a compound of the invention sufficient to inhibit the activity of PTP in said mammal. In some embodiments, the invention provides methods of inhibiting PTP activity in a human by contacting said human with an amount of a compound of the invention sufficient to inhibit the activity of PTP in said human. A nucleic acid ligand of the invention useful for such methods may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

The invention further provides methods of modulating PTP1B activity by contacting PTP1B with an amount of a compound of the invention sufficient to modulate the activity of PTP1B. Modulation can be inhibition or activation PTP1B activity. In some embodiments, the invention provides methods of inhibiting PTP1B activity by contacting PTP1B with an amount of a compound of the invention sufficient to inhibit the activity of PTP1B. In some embodiments, the invention provides methods of inhibiting PTP1B activity in a solution by contacting said solution with an amount of a compound of the invention sufficient to inhibit the activity of PTP1B in said solution. In some embodiments, the invention provides methods of inhibiting PTP1B activity in a cell by contacting said cell with an amount of a compound of the invention sufficient to inhibit the activity of PTP1B in said cell. In some embodiments, the invention provides methods of inhibiting PTP1B activity in a tissue by contacting said tissue with an amount of a compound of the invention sufficient to inhibit the activity of PTP1B in said tissue. In some embodiments, the invention provides methods of inhibiting PTP1B activity in an organism by contacting said organism with an amount of a compound of the invention sufficient to inhibit the activity of PTP1B in said organism. In some embodiments, the invention provides methods of inhibiting PTP1B activity in an animal by contacting said animal with an amount of a compound of the invention sufficient to inhibit the activity of PTP1B in said animal. In some embodiments, the invention provides methods of inhibiting PTP1B activity in a mammal by contacting said mammal with an amount of a compound of the invention sufficient to inhibit the activity of PTP1B in said mammal. In some embodiments, the invention provides methods of inhibiting PTP1B activity in a human by contacting said human with an amount of a compound of the invention sufficient to inhibit the activity of PTP1B in said human. A nucleic acid ligand of the invention useful for such methods may comprise a sequence as shown in Table 3. In other embodiments, the nucleic acid ligand comprises a sequence exhibiting at least about 60% sequence identity to any of the sequences shown in Table 3. Alternatively, the polynucleotide comprises a sequence exhibiting at least about 70%, 80%, 90% or 95% sequence identity to any of the sequences shown in Table 3.

Nucleic acid ligands of the invention may have several advantages when compared to antibodies or small molecules for use in therapeutic and diagnostic applications. Nucleic acid ligands are generally nonimmunogenic and highly stable, especially when modified for RNase resistance often resulting in earlier clinical application. As well as being affected less by the intracellular environment, these properties may lead to easier and more reproducible production possibilities. Complementary sequences can be easily constructed that anneal to a nucleic acid ligand offering the possibility of effective, specific antidotes that make tighter regulation possible. Additionally, production of nucleic acid ligands is cost-effective and well understood.

In some embodiments, the methods of the invention involve the administration of the nucleic acid ligands provided herein. In some embodiments, the nucleic acid ligands provided herein are administered in a single dose. In some embodiments, the nucleic acid ligands provided herein are administered in multiple doses. Dosing may be about once, twice, three times, four times, five times, six times, or more than six times per day. In some embodiments, dosing may be about once a month, once every two weeks, once a week, or once every other day, or any other suitable interval. Administration of the nucleic acid ligands provided herein may continue as long as necessary. In some embodiments, a nucleic acid ligand of the invention is administered for more than about 1, 2, 3, 4, 5, 6, 7, 14, or 28 days. In some embodiments, a nucleic acid ligand of the invention is administered for less than about 28, 14, 7, 6, 5, 4, 3, 2, or 1 day. In some embodiments, a nucleic acid ligand of the invention is administered chronically on an ongoing basis, e.g., for the treatment of chronic effects.

An effective amount of the nucleic acid ligands provided herein may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

The nucleic acid ligands described herein may be administered in dosages. Dosing ranges for therapeutic agents are known in the art. It is also known in the art that due to intersubject variability in therapeutic agents, pharmacokinetics, individualization of dosing regimen is necessary for optimal therapy. Dosing for the nucleic acid ligands provided herein may be found by routine experimentation.

In some embodiments, the nucleic acid ligands are co-administered with a therapeutic agent. "Co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present. Administration of the therapeutic agent and the nucleic acid ligands described herein may be any suitable means. If the agents are administered as separate compositions, they may be administered by the same route or by different routes. If the agents are administered in a single composition, they may be administered by any suitable route. In some embodiments, the agents are administered as a single composition by oral administration. In some embodiments, the agents are administered as a single composition by transdermal administration. In some embodiments, the agents are administered as a single composition by injection.

The nucleic acid ligands provided herein may be used for the identification and quantitation of target protein in a biological sample. Consequently, diagnostic assays which examine PTP1B expression can be used in clinical contexts for the evaluation of diagnostic, prognostic and therapeutic aspects of patients suffering from diseases characterized by an aberrant expression of this molecule. A number of patents describe assays suitable for use with nucleic acid ligands of the invention, such as U.S. Pat. Nos. 6,261,783; 6,531,286; 6,680,377; 7,074,586; and 6,287,765. For example, such assays can be tailored to measure PTP1B levels in an individual relative to PTP1B levels in a control population. The method entails contacting a sample suspected of containing PTP1B from the individual with a nucleic acid ligand of the invention and measuring the strength of the binding interaction. One can then determine the PTP1B levels in the individual relative to the levels in a control population. In another example, nucleic acid ligands labeled with fluorescent molecules may be used in flow cytometric methods to detect the level of PTP1B protein in cells. In yet another example, fluorescently-labeled nucleic acid ligands of the invention may be immobilized on a glass surface to generate ligand-dependent signals based on the interaction with target protein. Such signals may be detected, for instance, by evanescent wave fluorimetry.

Pharmaceutical Compositions and Formulations

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. When the compounds described herein and other therapeutic agents are used in combination, both components may be mixed into a preparation or both components may be formulated into separate preparations to use them in combination separately or at the same time. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins 1999).

The present invention encompasses any pharmaceutically acceptable salt, ester, salt of an ester, pro-drug or other derivative of a nucleic acid ligand of this invention which, upon administration to a recipient, is capable of providing (directly or indirectly) a nucleic acid ligand of this invention. For example, pharmaceutically acceptable derivatives may be used which increase the bioavailability of the compounds of the invention when administered to a mammal (e.g., by increasing absorption into the blood of an orally administered compound) or which increases delivery of the active compound to a biological compartment (e.g., the brain or lymphatic system) relative to the parent species. Some pharmaceutically acceptable derivatives include a chemical group which increases aqueous solubility or active transport across the gastrointestinal mucosa, such as PEGylation or linkage to polypeptides which may increase cellular or tissue permeability.

Provided herein are pharmaceutical compositions comprising a nucleic acid ligand of the invention and a pharmaceutically acceptable diluent(s), excipient(s), or carrier(s). In certain embodiments, the compounds described are administered as pharmaceutical compositions in which nucleic acid ligands of the invention are mixed with other active ingredients, as in combination therapy. Encompassed herein are all combinations of actives set forth in the combination therapies section below and throughout this disclosure. In specific embodiments, the pharmaceutical compositions include one or more nucleic acid ligands of the invention.

A pharmaceutical composition, as used herein, refers to a mixture of a nucleic acid ligand of the invention with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of nucleic acid ligands of the invention provided herein are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more nucleic acid ligands of the invention are formulated in an aqueous solution. In specific embodiments, the aqueous solution is selected from, by way of example only, a physiologically compatible buffer, such as Hank's solution, Ringer's solution, or physiological saline buffer. In other embodiments, one or more nucleic acid ligand of the invention is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein, including nucleic acid ligands of the invention are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dye-stuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the nucleic acid ligands of the invention are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the nucleic acid ligands of the invention are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the nucleic acid ligands of the invention is accomplished by means of iontophoretic patches and the like. In certain embodiments, transdermal patches provide controlled delivery of the nucleic acid ligands of the invention. In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the nucleic acid ligands of the invention are formulated for administration by inhalation. Various forms suitable for administration by inhalation include, but are not limited to, aerosols, mists or powders. Pharmaceutical compositions are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the nucleic acid ligands of the invention are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a nucleic acid ligand of the invention are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one nucleic acid ligand of the invention described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one nucleic acid ligand of the invention illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of the invention. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Kits

Kits including reagents useful for performing the methods described herein are also provided. In some embodiments, a kit includes reagents including a nucleic acid ligand, buffer, and other components as described herein. The nucleic acid ligand may be fluorescently or radioactively labeled. The kit may optionally contain one or more of the following: one or more of the nucleic acid ligands of the invention, instructions for the use of the kit, and additional reagents such as buffers. The components of a kit can be retained by a housing. Instructions for using the kit to perform a described method can be provided with the housing, and can be provided in any fixed medium. The instructions may be located inside the housing or outside the housing, and may be printed on the interior or exterior of any surface forming the housing that renders the instructions legible. A kit may be in multiplex form for testing a plurality of test samples and/or a plurality of agents.

Figure 12:
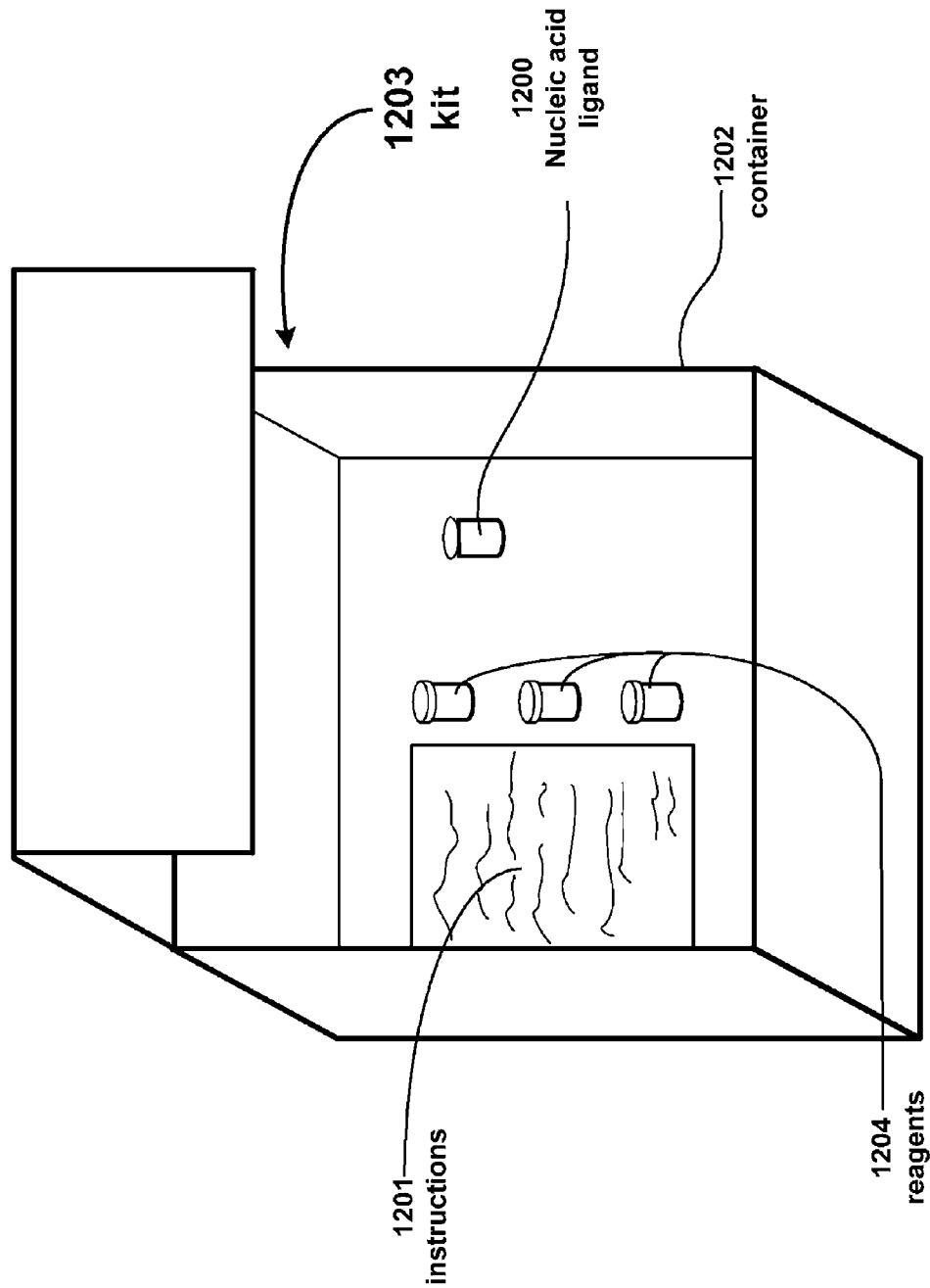
FIG. 12 is a block diagram showing a representative example of a kit.

As described herein and shown in FIG. 12, in certain embodiments a kit 1203 can include a container or housing 1202 for housing various components. As shown in FIG. 12, and described herein, in one embodiment a kit 1203 including one or more nucleic acid ligands 1200, and optionally reagents 1204 are provided. As shown in FIG. 12, and described herein, the kit 1203 can optionally include instructions 1201. Other embodiments of the kit 1203 are envisioned wherein the components include various additional features described herein.

EXAMPLES

Example 1

Materials

The human protein tyrosine phosphatases, 1B (PTP1B) and T-cell (TC-PTP), were prepared as described in Stuible et al (2007) Chembiochem 8(2), 179-186. They consisted of the 321- and 354-residue catalytic domains respectively with GST tags added for purification. In addition, PTP1B with an amino-terminal $His_6$ tag, purchased from R&D systems (R&D Systems, Minneapolis, Minn., 1366-PT-050, MW 37839), was used for phosphatase assays and comparison. Radiolabelled $\gamma$-$^{32}$P ATP and $\alpha$-$^{32}$P UTP were purchased from Perkin-Elmer. All other reagents were molecular-biology grade from commercial suppliers. All solutions were made using RNase-Free water (Invitrogen) and RNase-free procedures were employed.

Example 2

Initial Pool

An initial pool of single-stranded DNA (ssDNA) used the N30 sequence described in Ausubel, F. M. (ed) (2001), Current protocols in molecular biology, John Wiley & Sons, Inc., New York and shown in Table 2. This sequence comprises a 30-nucleotide random region with approximately equal distribution of each possible nucleotide. Fixed regions on either end provided priming sites, restriction sites, and a T7 promoter region. Integrated DNA Technologies synthesized the pool and matching primers as ssDNA. The complementary strand was synthesized by Klenow extension. The DNA was then transcribed using Ambion MegaShortScript transcription kits. The resulting oligomers were purified using a denaturing PAGE with the desired band visualized using UV-shadowing and then excised, eluted, and precipitated in ethanol. The initial SELEX round was carried out using 40 μg of 80-nucleotide RNA representing approximately $5 \times 10^{13}$ distinct sequences.

Example 3

Selection of Nucleic Acid Ligands

SELEX procedures were modeled after those described in Ausubel, F. M. (ed) (2001), Current protocols in molecular biology, John Wiley & Sons, Inc., New York; Kenan, D. J., and Keene, J. D. (1999) Methods Mol Biol 118, 217-231. In vitro selection was performed in a binding buffer consisting of 20 mM HEPES, 5 mM $MgCl_2$, and 125 mM NaCl at pH 7.2. The selection employed Millipore 0.45 μm HAWP nitrocellulose filters driven by an applied vacuum of approximately 130 mmHg. The first round of selection began with duplicate negative selections to eliminate filter-binding species. Immediately prior to use, the RNA was preheated to 75° C. for 3 minutes and allowed to cool to room temperature to allow the RNA to fold into its most stable conformation(s). Each pre-filtering duplicate used 20 μg of RNA suspended in 100 μl of binding buffer, which was passed through pre-washed filters and then followed by washing with another 100 μl of binding buffer. After the pre-filtering, 20 μl of each sample was retained as a control and 180 μl from each pre-filter was combined and mixed with 30 μg of PTP1B-GST giving an RNA:protein molar ratio of 1.8:1. The mixture was vortexed, and allowed to incubate at room temperature for 60 minutes. The solution was then passed through duplicate filters followed by three equal washes with binding buffer. The filters were collected and eluted twice for 5 minutes each at 90° C. in a 7M Urea, 3 mM EDTA, 100 mM sodium citrate elution buffer. Residual peptide fragments were then removed using a phenol-chloroform extraction followed by a chloroform extraction. The selected RNA was precipitated using an equal volume of isopropanol and then run on a 10% denaturing polyacrylamide gel and the relevant band was visualized using UV-shadowing and excised. The gel fragments were eluted overnight in water at 37° C. and the RNA was precipitated from the supernatant with 2.5-volumes of ethanol containing 0.3M NaCl. The pellet was resuspended in Ambion RNA Storage Solution (1 mM sodium citrate, pH 6.4) at approximately 1 µg/µl.

Reverse transcription was performed using Qiagen Sensi-Script RT kits. Reverse transcription was performed in duplicate on each of 4 samples; the two duplicates of selected RNA, the negative-select filter wash-through, and a no-RNA control. After incubating the RT reaction 60 minutes at 37° C., it was added to a PCR mix consisting of Bioron "Incomplete" PCR buffer, 0.2 mM dNTPs, 2 µM forward and reverse primers, 1.5 mM MgCl$_2$, and 5 U/µl Bioron Taq (#101005). Seven cycles of PCR were conducted with a cycle of 45 s@94° C., 60 s@55° C., 90s@72° C. The resulting DNA was then quantified using a Qubit™ dsDNA BR (Invitrogen) assay and PCR was continued for two more cycles. The samples were precipitated with ethanol and resuspended at approximately 1 µg/µl in TE buffer at pH 8.0. The resulting DNA was quantified using a Qubit dsDNA BR assay and verified for size and purity on NuSieve GTG 4% agarose gels.

For subsequent rounds of SELEX the same procedure as above was used with the following changes. In each round approximately 200 ng of the amplified DNA template were transcribed using Ambion MegaShortScript™ and then purified using Ambion NucAway spin columns to produce approximately 50 µg of RNA. Selection was carried out as above using duplicate selections at each round and followed by three equal washes of the filters prior to elution. The RNA:target ratio was modified at Round 4 to increase the stringency of selection and was then decreased for subsequent rounds to an intermediate ratio as shown in Table 1. Except for the initial selection round, Glycoblue was added to the RNA before precipitation to aid in the recovery of the pellet. After the initial seven cycles of PCR, the number of additional PCR cycles were adjusted during each round to yield 1-2 µg of DNA. Table 1 shows the quantities of RNA and PTP1B used in SELEX rounds per duplicate.

TABLE 1

Quantities of RNA and PTP1B used in SELEX rounds per duplicate.

| SELEX Round | RNA (µg) | PTP1B (µg) | RNA:Target (mole ratio) | PCR Cycles |
|---|---|---|---|---|
| 1 | 20 | 30 | 1.5 | 9 |
| 2 | 2.5 | 1.9 | 3.1 | 22 |
| 3 | 2.5 | 1.9 | 3.1 | 14 |
| 4 | 34 | 1.0 | 84 | 16 |
| 5 | 14.6 | 1.9 | 18 | 12 |
| 6 | 10.4 | 1.9 | 12.7 | 11 |
| 7 | 9.9 | 1.9 | 12.2 | 13 |
| 8 | 9.4 | 1.7 | 12.7 | 7 |
| 9 | 6.3 | 1.7 | 8.5 | 12 |

Example 4

Radiolabelled SELEX

In parallel with the cold SELEX performed above, some rounds of the SELEX were run in parallel using RNA labeled during transcription using α-$^{32}$P UTP. For these rounds the retained DNA from each round was transcribed in the presence of α-$^{32}$P UTP. This RNA was then used for one round of the same filtering steps used in the main selection. Each sample was pre-filtered and then separately filtered in the presence of 200 nM and 400 nM of the PTP1B target. The filters and wash-through were placed in liquid scintillation fluid and radioactivity was measured for 60 seconds on a RackBeta™ 1219 liquid scintillation counter.

Example 5

Binding Assays

Binding assays were carried out in triplicate at 12 different PTP1B concentrations using a Schleicher & Schuell Milliblot™ apparatus with 0.45 µm BioRad TransBlot® nitrocellulose layered on top of a Hybond™-N+nylon transfer membrane. Radiolabelled RNA at 100-500 pM was heated to 75° C. for 3 minutes then cooled to room temperature before mixing with a 2× serial dilution of the target and also a no-target control. 150 µL of the mixtures at each of the 12 enzyme concentrations were pre-incubated at room temperature for 60 minutes before applying to the pre-washed membrane to allow the RNA complex to reach equilibrium (Waley, S. G. (1993) The Biochemical journal 294 Pt 1, 195-200). Following addition of 40 µL per well of each mixture to three separate wells of the Milliblot™ apparatus, the filter was washed 3 times. The dilutions and all washes used the binding buffer described above. Activity of the filters was measured using a FujiFilm BAS-1800II phosphorimager and relative density used to estimate the fraction of radiolabelled RNA retained on the nitrocellulose and nylon membranes. Since RNA does not typically bind to nitrocellulose, but is trapped by the nylon membrane, the ratio of densities provides a measure of the fraction of the RNA bound to the target.

Example 6

Cloning and Sequencing

The dsDNA from the final SELEX pool was ligated into a Promega pGEM®-T vector using the manufacturer's protocol with positive and negative controls and then transformed into dh5a competent cells. Colonies were incubated for 16 hours on LB/Ampicillin/IPTG/X-Gal plates and ratios of blue/white colonies were verified. Twenty clones were picked and incubated overnight in LB medium. An Invitrogen Miniprep™ kit was used to purify the DNA, which were then sequenced by the McGill Genome Center. Possible secondary structures of RNA were modeled using the unafold program (Markham, N. R., and Zuker, M. (2005) Nucleic Acids Res 33 (Web Server issue), W577-581).

Example 7

Phosphatase Assays Using the Nucleic Acid Ligands of the Invention

The following in vitro assay procedure may be employed to determine the level of activity and effect of the different compounds of the present invention on one or more PTPs. Similar assays can be designed along the same lines for any PTP using techniques well known in the art.

Activity of phosphatases was measured using Invitrogen's EnzChek™ Acid Phosphatase assay kit with 6,8-difluoro-4-methylumbelliferyl phosphate (DiFMUP) as the substrate (Montalibet et al (2005) Methods 35(1), 2-8). Assays were carried out in the binding buffer as described above with the addition of 3 mM DTT and 0.1 mg/ml BSA in 100 µl wells. In addition, assays were carried out using 20 mM NaCl concentration instead of 125 mM. Although the latter concentration, which was also used for selection, may be more representative of ionic strength in the cell, the lower concentration results in increased phosphatase activity allowing better identification of effects. For assays with the nucleic acid ligand inhibitor, the nucleic acid ligand and phosphatase were mixed and allowed to incubate at room temperature 20-30 minutes before addition of DiFMUP. Fluorescence (358 nm/455 nm) was measured at 30 s intervals using a Thermo Scientific VarioSkan® multimode plate reader.

Example 8

Active Site Modifications of the Nucleic Acid Ligands of the Invention

Once sequences for the evolved nucleic acid ligands were determined, sequence modifications were probed for inhibitory properties. For each modification, ssDNA was synthesized including a T7 promoter region. This was annealed to a complementary promoter and used to synthesize RNA using a MegaShortScript™ transcription kit. This was followed by phenol-chloroform extraction, chloroform extraction and then precipitation in 0.3M sodium acetate with 2 volumes of ethanol. Phosphatase assays as described above were used to measure the effect of the modifications on inhibition.

Example 9

Selection Progress

In vitro selection began with a random pool of approximately $5 \times 10^{13}$ distinct RNA molecules with an average of 17 copies each. The amount of RNA and PTP1B-GST and the estimated yield of rounds 0, 2, 4, 6, 8, and 9 as determined by parallel radiolabelled selections, varied in each round as shown in Table 1. The ratio of RNA to target was modified at round 4 to increase the stringency of selection and was then decreased for subsequent rounds to an intermediate value. For rounds 0, 2, 4, 6, 8, and 9, parallel radiolabelled selection filtering was performed using 0, 200 nM and 400 nM final concentration of PTP1B enzyme. The ratio of filter radioactivity counts to the total of wash-through plus filter stayed below 1% for the first five rounds of selection independent of whether PTP1B proteins were present. For the subsequent rounds, the ratio climbed sharply to 35% in the presence of PTP1B at either concentration. This is indicative of the presence of a significant fraction of RNA that binds to the target. After eight rounds of selection the bound percentage stabilized at 30-35% while binding in the absence of PTP1B stayed below 1%. Details of the selection are shown in FIG. 1. The maximum bound percentage of 35% was the same at both 200 nM and 400 nM of PTP1B. Thus, the fact that less than 100% was retained is not likely due to the binding strength between the RNA and the protein. Rather, there may be present in the mixture radiolabelled RNA fragments or free nucleotides that do not bind to the nitrocellulose and lower the overall percentage bound.

After 8 rounds of SELEX, cloning and sequencing was performed on 20 clones, of which 19 were successfully sequenced. From these, three distinct sequences were found. The sequences of the initial pool and the clones are shown in Table 2.

TABLE 2

Sequences of initial pool and of clones after round 8. For the clones, the count is the number of clones with an identical sequence out of a sample of 20.

| ID | Sequence of Random Region | Number of times identified |
|---|---|---|
| N30 | GGGAAUGGAUCCACAUCUACGAAUUC*-------------N30--------------*UUCACUGCAGACUUGACGAAGCUU | |
| C13 | GGGAAUGGAUCCACAUCUACGAAUUC*UGUGAUCAAUUUGGCAAUCCGCCACACGAG*UUCACUGCAGACUUGACGAAGCUU | 16 |
| C9 | *------U--------------------U--* | 1 |
| C7 | GGGAAUGGAUCCACAUCUACGAAUUC*UCUCGCAGGCAAGCUAACUGAGAUCAC  *UUCACUGCAGACUUGACGAAGCUU | 2 |

The C9 clone, which was only observed once, is very similar to the prevalent C13 sequence with two base substitutions. The dominant sequences, C13 and C7, were used to resynthesize ssDNA and to produce single-sequence RNA using in-vitro transcription. In addition, as will be explained further below, a 42-nucleotide segment of the C13 nucleic acid ligand was also synthesized and used for subsequent binding and inhibition experiments. This is referred to as C13M21.

Example 10

Binding Assay

Figure 2:
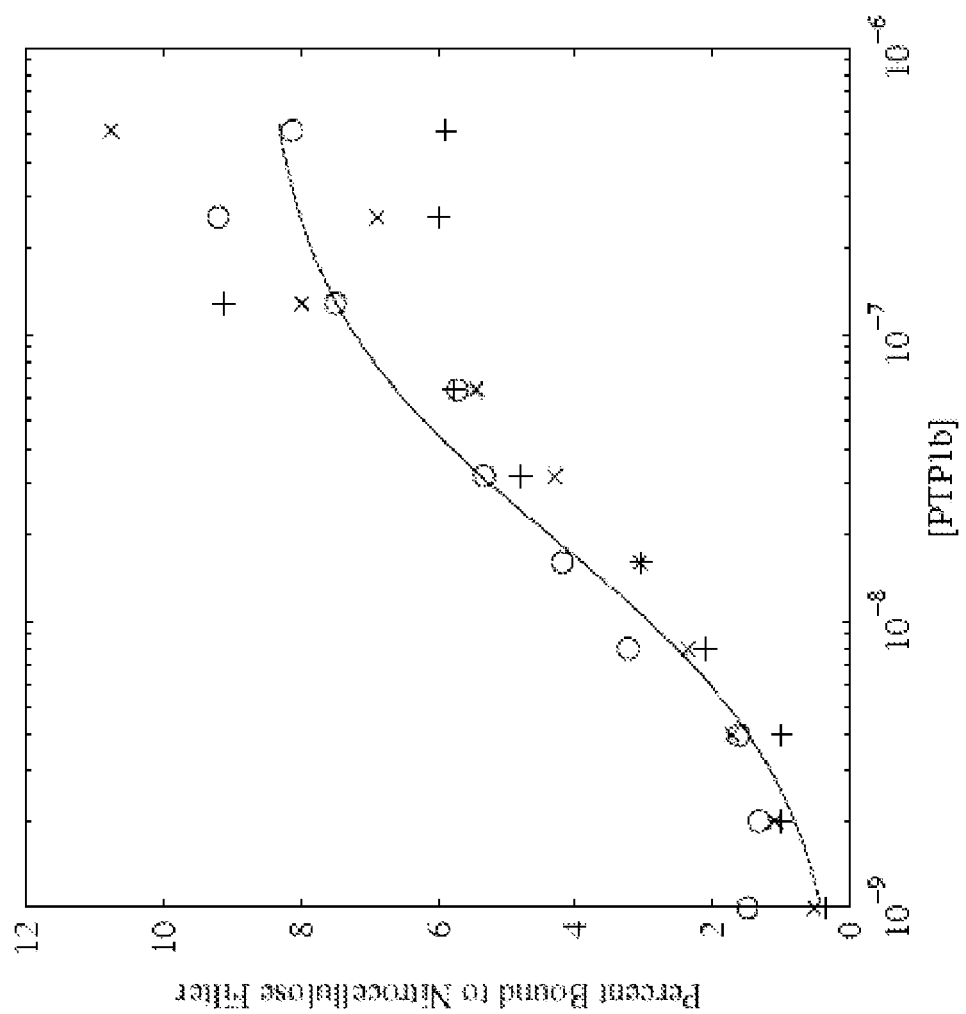
FIG. 2 shows a binding assay of C13M21 at 2 nM concentration performed in triplicate. PTP1B concentration was varied from 1 nM to 512 nM, mixed with the radiolabelled RNA, and allowed to incubate 60 minutes before filtering. The percent of total activity retained on a nitrocellulose membrane is shown. The open circles are the averages over the triplicates with error bars showing the extremes. The solid line is a nonlinear fit to a first-order binding reaction with the maximum binding as an extra free variable, $$p = \frac{p_{max}[PTP1b]}{K_d + [PTP1b]}.$$

A binding assay with a concentration of 2 nM of the radiolabelled C13M21 nucleic acid ligand against PTP1B-GST was performed with the protein concentration ranging from 1 nM to 512 nM in a 2:1 serial dilution. FIG. 2 shows the fraction of the radiolabelled nucleic acid ligand bound to the nitrocellulose filter for each protein concentration. A nonlinear fit of these data using the MATLAB software program estimates the $K_d$ of the nucleic acid ligand as 28 nM. As was discussed above, the maximum binding observed when using the single filter apparatus for selection was ~35%. This difference in maximum binding for the two procedures may be due to differences in amount of washing and different filter surface areas.

Example 11

Measurement of Nucleic Acid Ligand Inhibitor Properties

The $K_m$ of PTP1B was measured using an EnzChek phosphatase assay kit with DiFMUP as the substrate as follows. Measurements of the initial slope of fluorescent activity were made in duplicate using 11-step serial dilutions from 1 µM to 200 µM of DiFMUP. The same buffer was used as for selection. In addition, measurements were made in an experiment with duplicates using a buffer differing in that the NaCl was 20 mM instead of 125 mM. For the assays, commercially produced PTP1B from R&D Systems was used at 1 nM final concentration for the 125 mM NaCl condition and at 250 pM for the 20 mM NaCl condition. A nonlinear fit to the Michaelis-Menten equation using the MATLAB software program gives an estimated $K_m$ of 25.5 µM for the PTP1B at 125 mM NaCl. These data and fit are shown as the upppercurves in the double-reciprocal Lineweaver-Burk plot of FIG. 3. Similarly, a $K_m$ of 5.5 µM was found when using a buffer with 20 mM NaCl. These agree well with other published results of approximately 5 µM for conditions similar to the tested low-ionic strength conditions (Montalibet, J., et al (2005) Methods 35(1), 2-8).

Figure 3:
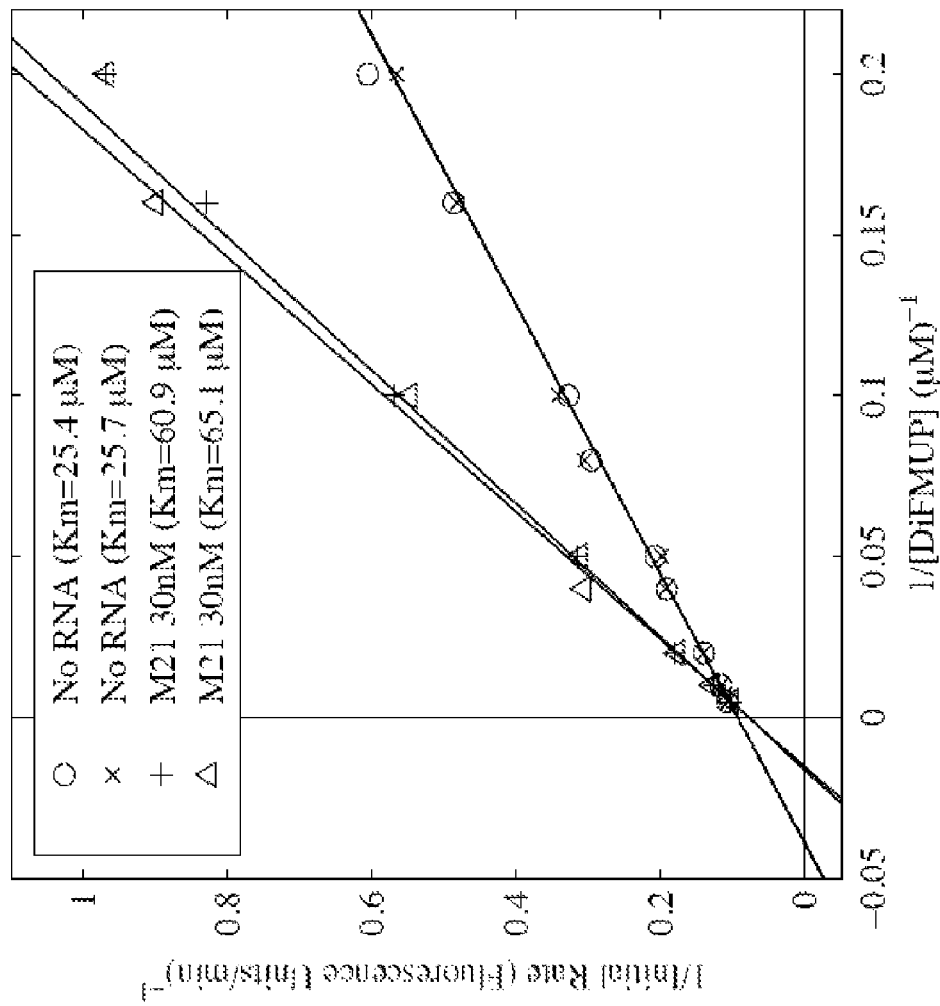
FIG. 3 displays a Lineweaver-Burk plot of the initial rate of product formation measured by fluorescence with and without C13M21 present for varying concentrations of DiFMUP substrate in buffer with 125 mM NaCl. Two independent experiments were performed for each condition. Solid lines are nonlinear fits of the untransformed data to the Michaelis-Menten model, performed independently for each experiment. The average of the fitted $V_{max}$ was 10.6 FU/min when no nucleic acid ligand was present and 12.7 FU/min for the M21 nucleic acid ligand.

In parallel with a no-RNA control, the activity in the presence of 30 nM C13M21 was measured in duplicate for varying concentrations of DiFMUP. FIG. 3 shows these data for the 125 mM NaCl condition with a nonlinear fit to the Michaelis-Menten equation superimposed on each of the experiment's results. Fitting of the data in the presence of C13M21 gave a $K_m$* of 63 µM, which equates to a $K_i$ of 20 nM. The fitted $V_{max}$ in the presence of the inhibitor was equal to or slightly greater than the no-RNA $V_{max}$, indicating the presence of competitive inhibition.

Figure 4:
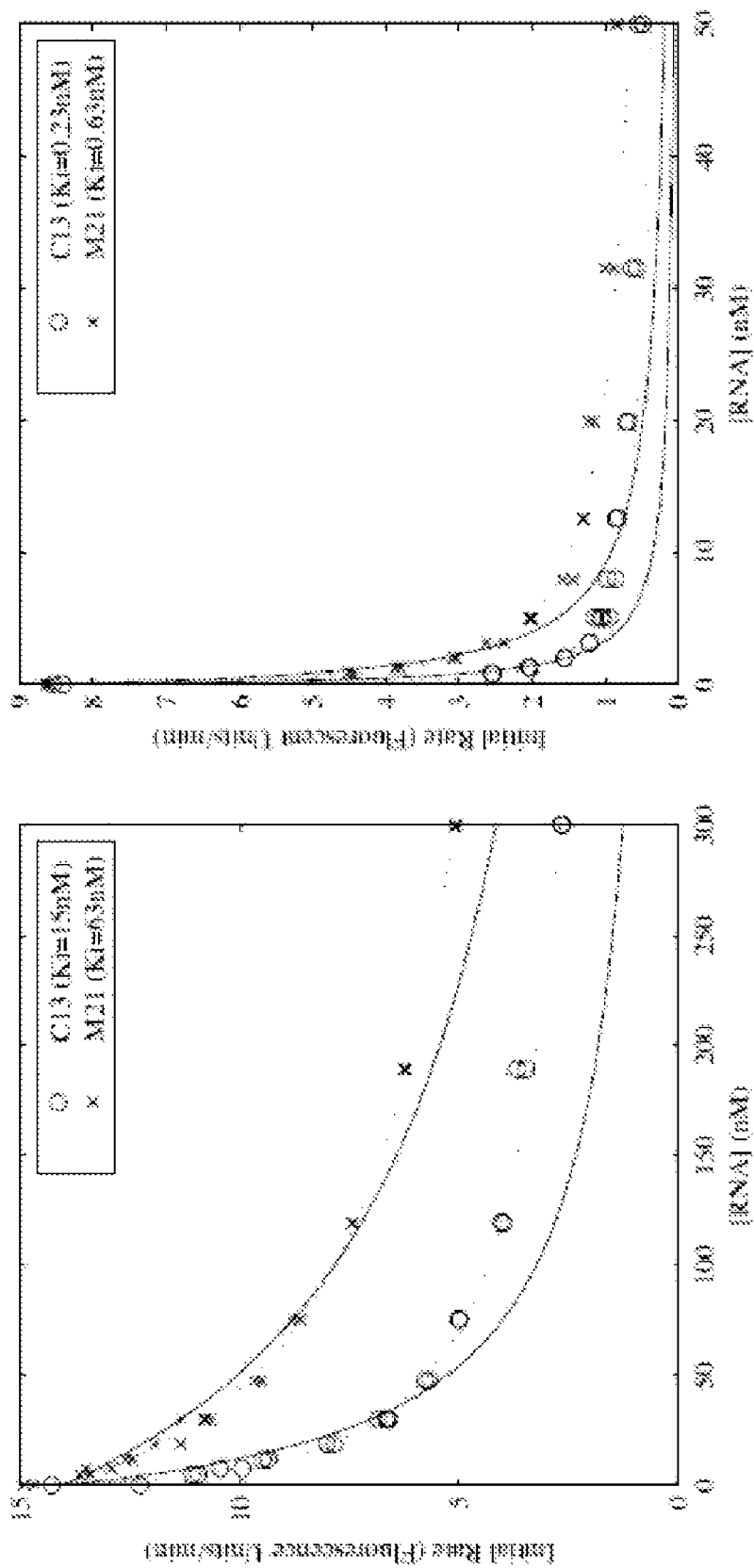
FIG. 4 indicates the IC50 of C13M21 nucleic acid ligand inhibiting 0.5 nM PTP1B. The left plot is at 125 mM NaCl concentration with 25 μM DiFMUP and the right plot is at 20 mM NaCl with 5 μM DiFMUP. In each plot the initial rate of product formation is shown as a function of concentration of two nucleic acid ligands; the full-length C13 and the reduced C13M21, each in duplicate. Solid lines are fits to the Michaelis-Menten competitive inhibition model.

To further refine the estimate of $K_i$, an assay was run at a fixed DiFMUP concentration of 20 µM with the C13M21 and the full-length C13 nucleic acid ligand, each premixed with the PTP1B at mM in the 125 mM NaCl buffer. The left panel of FIG. 4 shows the resulting measured activity at nucleic acid ligand concentrations ranging from 0.5 nM to 300 nM. Nonlinear fitting gives an estimate of the $IC_{50}$ of 30 nM. Based on a $K_m$ of 25 µM, and assuming competitive inhibition, this gives a $K_i$ of 45 nM for C13M21 and a $K_i$ of 7 nM for the full-length nucleic acid ligand at 125 mM NaCl concentration.

Similar assays with 20 mM NaCl and 5 µM DiFMUP are shown in the right panel of FIG. 4 and give a $K_i$ of 300 pM for C13M21 and less than 100 pM for C13. However, with a PTP1B concentration of 500 pM, the measurement may be limited by the ratio of enzyme to inhibitor and the $K_i$ may be even lower (Montalibet, J. et al (2005) Methods 35(1), 2-8; Henderson, P. J. (1972) The Biochemical journal 127(2), 321-333).

The data above systematically differ from the Michaelis-Menten model at the higher end of the nucleic acid ligand concentrations where the observed inhibition is less than would be expected with the fitted parameters. It was observed that a reaction with second-order dependence on the inhibiting nucleic acid ligand, such as a dimerization, would give rise to the observed results. As the nucleic acid ligand concentration increases this reaction would become dominant, limiting the nucleic acid ligand available to inhibit the PTP1B. Adding this to Michaelis-Menten model results in the dotted line shown in FIG. 4, which fits the observed data more closely. To verify that the inhibition is reversible, RNase A was added to an assay after inhibition was observed using DiFMUP for 10 minutes. At all concentrations of RNase tested, inhibition was completely reversed as soon as measurements were resumed within 60 seconds after addition.

Assays similar to the above but using the initial RNA pool in place of C13M21 were also tested to verify that the observed results were not due to non-specific RNA. In all cases these showed no measurable inhibition.

Example 12

Measurement of Nucleic Acid Ligand Binding Properties

Figure 5:
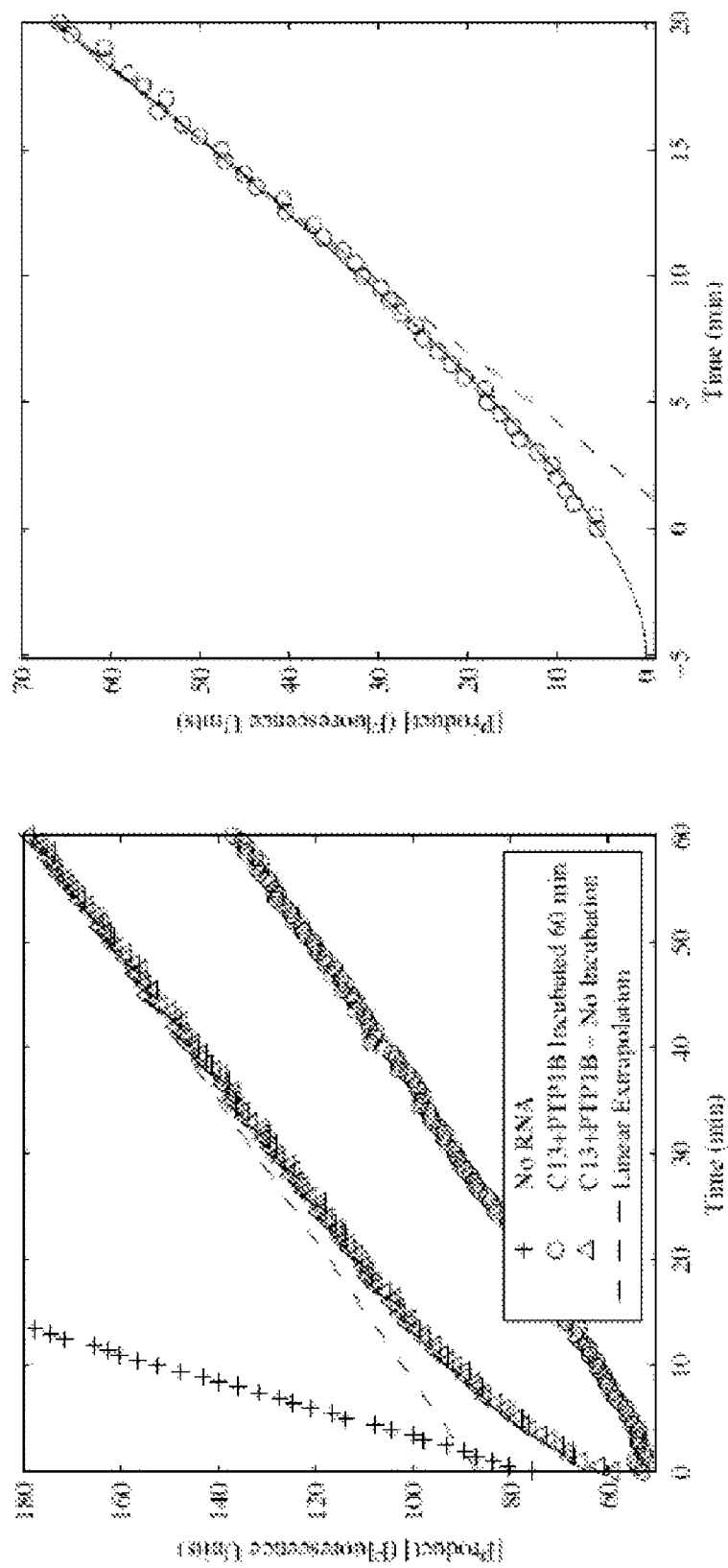
FIG. 5 shows slow binding and unbinding of the nucleic acid ligand of the invention. The left frame represents the first 60 minutes of a fluorescence progress curve with and without pre-incubation of the PTP1B and nucleic acid ligand. The solid line is an extrapolation of a linear fit to the data over times ranging from 40 to 120 minutes (data not shown from 60 to 120 minutes remains linear), illustrating the binding of the nucleic acid ligand over the first 30 to 50 minutes. The right frame shows the progress curve of fluorescence after adding pre-incubated PTP1B and nucleic acid ligand to a DiFMUP substrate. Each point is the average fluorescence of two duplicates at 30-second intervals. The dotted line is a linear extrapolation of the points over the period 20-45 minutes. The solid line is the best fit to the exponential decay model.

Inhibition of PTP1B by the C13M21 nucleic acid ligand appears to exhibit some "slow-binding" properties (Waley, S. G. (1993) The Biochemical journal 294 (Pt 1), 195-200; Garrido-del Solo, C et al (1999) Bio Systems 51(3), 169-180). FIG. 5 shows the progress curve of fluorescence activity in a 20 µM DiFMUP assay with 125 mM NaCl under three conditions: PTP1B alone, PTP1B mixed with the nucleic acid ligand immediately before beginning reading at T=0 minutes, and PTP1B mixed with the nucleic acid ligand and allowed to incubate 60 minutes before its addition to the DiFMUP substrate mix. In all cases the PTP1B concentration was 0.85 nM and the nucleic acid ligand concentration was 20 nM. The reaction rate decreases over the first 50 minutes for the condition in which there was no pre-incubation starting with a rate similar to that of the no-nucleic acid ligand condition. Thus, it appears that some time is required for the nucleic acid ligand to bind to the PTP1B target before inhibition occurs. It takes approximately 50 minutes before binding between the nucleic acid ligand and PTP1B is relatively complete at these concentrations.

There is also evidence that the converse, "slow-unbinding," is also occurring. The right frame of FIG. 5 shows the progress curve of fluorescence with 20 mM NaCl. PTP1B at 500 pM was mixed with 1.3 µM C13M21 and incubated 30 minutes. The PTP1B+RNA (180 µl) was then added to 20 DiFMUP for a final DiFMUP concentration of 5 µM and fluorescence measurements were begun within two minutes, as shown in FIG. 5. The rate of increase of fluorescence was initially low and increased over the first 10-20 minutes. By the time 20 minutes had elapsed, the rate stabilized at 3.6 fluorescent units/minute and remained constant for the duration of the experiment. Not wishing to be bound by theory, Applicants believe that during the first 10-20 minutes the substrate was displacing the RNA until equilibrium was reached. Since there is no observed delay in binding between PTP1B and the substrate when RNA is not present, this indicates that the RNA is being released slowly from the PTP1B. A nonlinear fit to the data assuming the velocity follows $v=v_s+(v_0-v_s)e^{-kt}$ yielded an estimate of the time constant k as 0.14 min$^{-1}$, and an initial velocity, $v_0$, close to zero. The rate after the initial equilibrium, but still early enough to assume low levels of product formation, $v_s$, was approximately 1.5 fluorescence units/minute, which was the same for the pre-incubated RNA.

Example 13

Selectivity of Inhibition by the Nucleic Acid Ligand

Since TC-PTP shares many similarities with PTP1B and is commonly inhibited by inhibitors of PTP1B, inhibition of TC-PTP by the C13M21 nucleic acid ligand was also measured. The $K_m$ of TC-PTP for DiFMUP as a substrate at concentrations ranging from 1.5 µM to 100 µM with the same 20 mM NaCl buffer used above was determined. A nonlinear fit of the data to the Michaelis-Menten equation estimated the $K_m$ under these conditions to be 5.7 µM.

Figure 6:
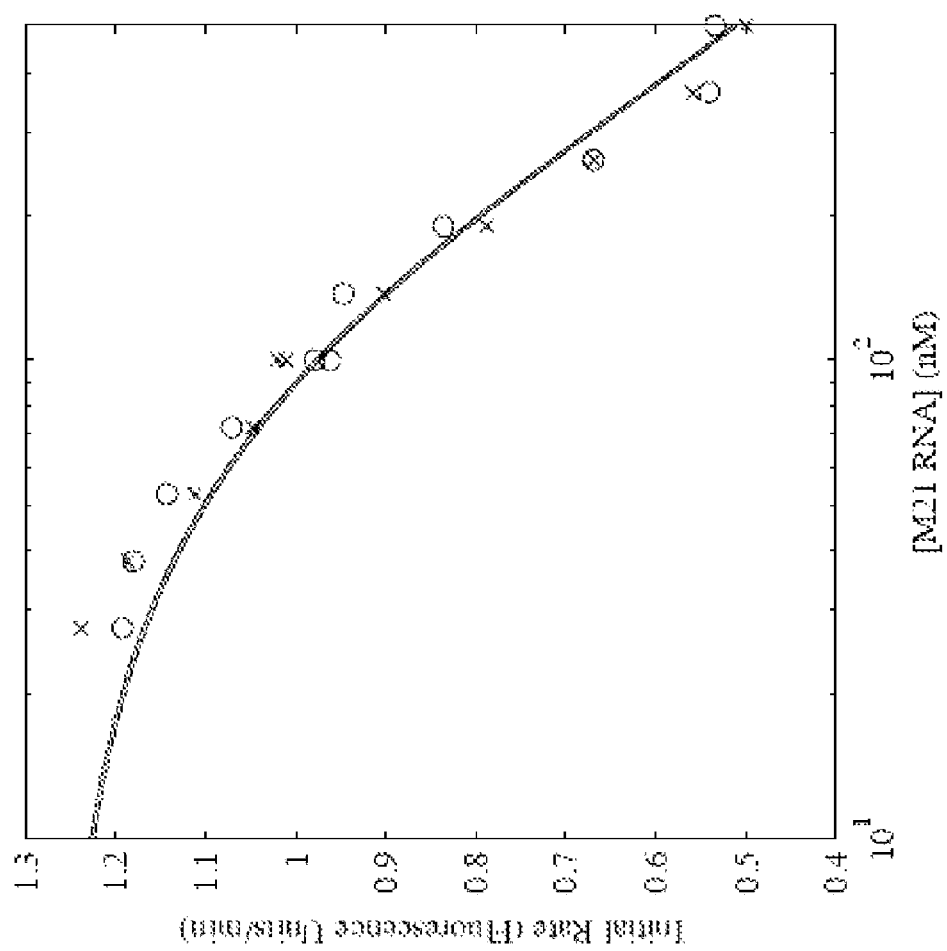
FIG. 6 displays the IC50 of C13M21 nucleic acid ligand inhibiting 0.2 nM TC-PTP in binding buffer with 20 mM NaCl and 6 μM DiFMUP. Solid lines are independent fits for each of two independent experiments to the competitive inhibition model, yielding estimates of $K_i$ of 166 nM and 168 nM.

FIG. 6 shows the effect of varying concentrations of the C13M21 nucleic acid ligand on a TC-PTP phosphatase assay with a fixed DiFMUP concentration of 6 µM. A fit of a nonlinear competitive inhibition model yields the lines shown in FIG. 6 and a predicted $K_i$ of 166 nM and 168 nM for the two independent experiments. Since the $K_i$ of PTP1B under similar conditions is approximately 600 pM, this indicates that TC-PTP is about 300× less sensitive to inhibition by C13M21.

Figure 7:
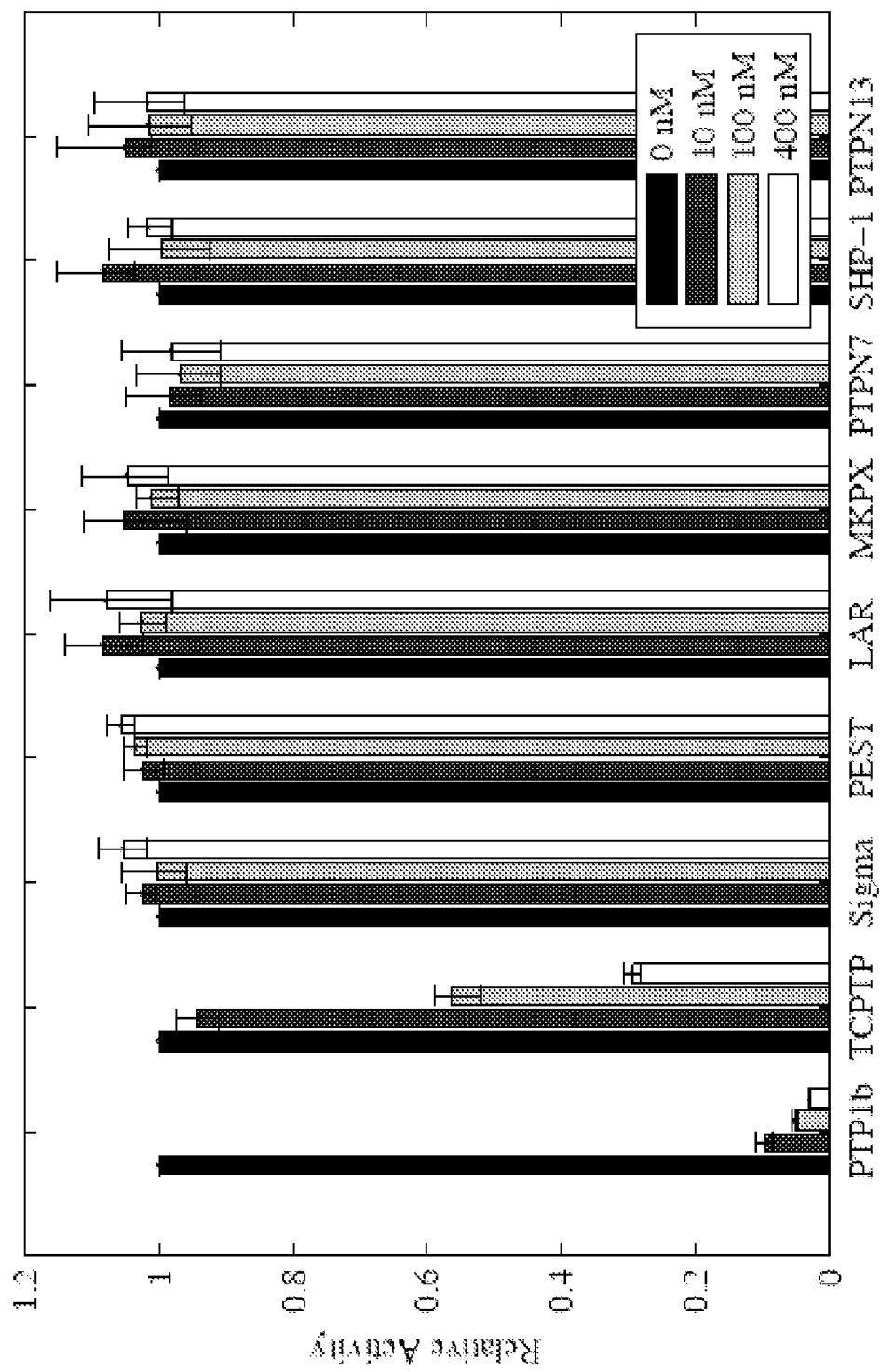
FIG. 7 illustrates the initial rate of product formation in the presence of various phosphatases in 5 μM DiFMUP relative to the initial rate with no nucleic acid ligand present. For each enzyme, nucleic acid ligand C13M21 concentrations of 0, 10, 100, and 400 nM are shown. Error bars on each column indicate the range of values obtained in 4 independent experiments.

Further studies measured whether any detectable inhibition of other phosphatases occurred at concentrations of the nucleic acid ligand up to 1000× the $K_i$ for PTP1B. The phosphatases TCPTP, Sigma, LAR, PEST, MKPX, PTPN7, SHP-1, and PTPN13 were produced in bacteria as GST fusion proteins. For each phosphatase, the activity and $K_m$ was measured using DiFMUP as the substrate in the same buffer as used above with a NaCl concentration of 20 mM. Inhibition was then measured at a substrate concentration of 5 µM with nucleic acid ligand concentrations of 0, 10, 100, and 400 nM. FIG. 7 depicts the inhibition relative to the no-nucleic acid ligand condition when averaged over two independent trials. None of the phosphatases other than TCPTP showed any measurable inhibition at these nucleic acid ligand concentrations. TCPTP observations were consistent with it being 300 times less susceptible to the nucleic acid ligand inhibition.

Example 14

Sequence Truncation and Modifications of the Nucleic Acids of the Invention

Figure 8:
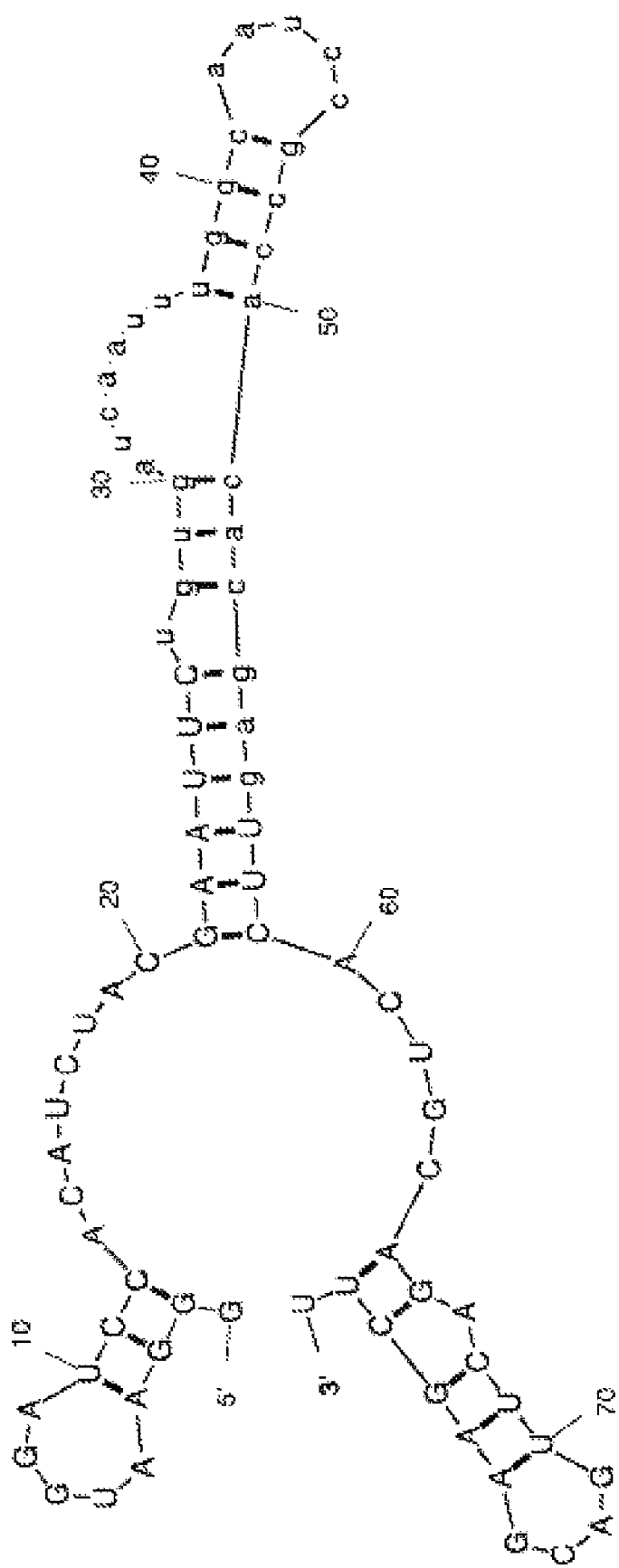
FIG. 8 is an expected secondary structure of the C13 RNA Nucleic acid ligand as predicted by the Unafold program. Lower case nucleotides were part of the originally random segment.

The unafold (Markham, N. R., and Zuker, M. (2005) *Nucleic Acids Res* 33 (Web Server issue), W577-581) program was used to predict the secondary structure of the C13 nucleic acid ligand and is shown in FIG. 8. Although unafold predicted many other structures with similar energy, most shared the same secondary structure in the region of nucleotides 21 through 59 and differed only in the folding and base-pairing between a few nucleotides in the outer regions. The initial pool contained a 30-nucleotide random region that spanned nucleotides 27 through 56. Thus it appears that the fixed region was used in forming the outer base-pairs of the long hairpin structure in the nucleic acid ligand. The first round of SELEX used $5 \times 10^{13}$ random oligonucleotides and there are $4^{30} = 10^{18}$ possible values for the random region. Assuming uniform distributions of the random regions, and no inadvertent loss of complexity, this leads to an average of 5 examples in the initial pool that differ in 3 or less positions from any other member and less than 0.19 on average that differ in 2 or less positions. Thus, one would expect that other similar nucleic acid ligand sequences differing in one or two nucleotides were not in the original pool and may also share the tight binding properties.

RNA nucleic acid ligands were then synthesized from segments of the 80-nucleotide C13 sequence to identify a minimal active nucleic acid ligand. Due to the mechanics of the T7 transcription, each RNA sequence commences with three Guanines if they were not already present at the beginning of the truncated sequence. The $K_i$ for each segment was estimated using DiFMUP phosphatase assays to determine if activity was maintained after the truncation. These assays were performed in two or more independent experiments for each sequence in 125 mM NaCl with 1 nM PTP1B and 25 µM DiFMUP. A sample of the pool generated after the third round of the SELEX, labeled S3T1, was also used for comparison. For each truncated nucleic acid ligand, the initial enzyme rate was measured for a nucleic acid ligand concentration of 40 nM and 200 nM in addition to the no nucleic acid ligand condition. The ratios of the initial rate with nucleic acid ligand present to the uninhibited rates are shown in Table 3. As the outer parts of the nucleic acid ligand are removed the inhibition is slowly reduced as reflected in an increase of the relative rates but some inhibition is maintained except for the M27 nucleic acid ligand for which there was no inhibition detected. The lack of inhibition by M27 is likely due to its lowest energy secondary structure having a different form than the relevant region of the longer nucleic acid ligands. The M28 nucleic acid ligand forms a structure that the above secondary structure model indicates forms a hairpin between the first 3 and last 3 nucleotides. Compared to this, the M27 has an additional TG at the beginning of one strand possibly causing other base-pairings that destroy the structure needed for binding to the PTP1B. These data indicate that the base-pairings from nucleotides 21-27 with those from 59-54 are not essential to the inhibition though they may improve the stability of the nucleic acid ligand and help ensure that it folds into the active conformation. Reducing the nucleic acid ligand further eliminates any detectable inhibition.

TABLE 3

Effect of truncation of C13 nucleic acid ligand on inhibition of PTP1B.

| Name | C13 Range | Sequence (5' to 3') | Relative Inhibition [RNA] = 40 nM | [RNA] = 200 nM |
|---|---|---|---|---|
| C13 | 1-80 | GGGAAUGGAUCCACAUCUAC GAAUUCUGUGAUCAAUUUGGCAAUCCGCCACACGAGUUC ACUGCAGACUUGACGAAGCUU | 0.42 ± 0.05 | 0.19 ± 0.02 |
| C13M21 | 21-59 | GGGAAUUCUGUGAUCAAUUUGGCAAUCCGCCACACGAGUUC | 0.63 ± 0.05 | 0.36 ± 0.03 |
| C13M23 | 23-57 | GGGAUUCUGUGAUCAAUUUGGCAAUCCGCCACACGAGU | 0.64 ± 0.02 | 0.33 ± 0.01 |
| C13M25 | 25-55 | GGGUCUGUGAUCAAUUUGGCAAUCCGCCACACGA | 0.84 ± 0.11 | 0.52 ± 0.05 |
| C13M27 | 27-53 | GGGUGUGAUCAAUUUGGCAAUCCGCCACAC | No inh. | |
| C13M28 | 28-53 | GGGUGAUCAAUUUGGCAAUCCGCCACAC | 0.79 ± 0.13 | 0.55 ± 0.01 |

TABLE 3-continued

Effect of truncation of C13 nucleic acid ligand on inhibition of PTP1B.

| Name | C13 Range | Sequence (5' to 3') | Relative Inhibition [RNA] = 40 nM | [RNA] = 200 nM |
|---|---|---|---|---|
| C13M29 | 28-52 | GGGUGAUCAAUUUGGCAAUCCGCCACA | 0.95 ± 0.06 | 0.91 ± 0.03 |
| C13M30 | 30-51 | GGGAUCAAUUUGGCAAUCCGCCAC | No inh. | |
| C13M38 | 38-50 | GGGUGGCAAUCCGCCA | No inh. | |
| C13M39 | 39-49 | GGGCAAUCCGCC | No inh. | |
| S3T1 | N/A | N30 Sequence | No inh. | |

The inhibition shown in this table, relative to a no RNA control, were estimated based on DiFMUP assays in buffer with 125 mM NaCl and the nucleic acid ligand at 40 nM and at 200 nM. Error estimates are standard deviations of results over multiple independent experiments.

The DiFMUP phosphatase assays used the C13M21 truncated nucleic acid ligand as the inhibitor, since this was a significantly smaller molecule with inhibition approaching that of the full-length nucleic acid ligand, C13.

Another group of modified nucleic acid ligands based on C13M21 were synthesized to verify the hairpins and base-pairings postulated by the secondary structure model. In each case a single base-pairing was tested by exchanging the two bases across the postulated pairing and then measuring the phosphatase inhibition using independent 20 μM DiFMUP assays with 50 nM of the modified RNA in the 125 mM NaCl buffer. A binary decision was made for each pairing based on whether the nucleic acid ligand with the swapped nucleotides exhibited any inhibition (activity less than 95% of the activity observed without an inhibitor). These results are summarized on the dot-plot shown in FIG. 10. Each point in this matrix represents a possible base-pairing as postulated by unafold at different relative energies as indicated. An "O" indicates that PTP1B inhibition is maintained when the corresponding pair is swapped. An X indicates that the swap results in no observed PTP1B inhibition. The filled dots are possible pairings that were not tested by swapping.

From the dot-plot, it appears that swaps across the postulated hairpin connecting nucleotides 21-30 with nucleotides 51-59 maintain phosphatase inhibition. However, all tested swaps outside this region result in loss of inhibitory properties, even those across the base-pairings postulated by the secondary structure shown in FIG. 9 between nucleotides 38-41 and 47-50.

Example 15

Single Base Modifications

Several single-base modifications of the M21 nucleic acid ligand were also tested to determine whether the changes would affect the level of inhibition. With reference to the postulated secondary structure shown in FIG. 9, the sequence at each position on the unpaired regions was modified at positions 31 through 37 and positions 42 through 46. At each of these positions RNA with the single replacement of the alternate purine or pyrimidine (A⇔G or C⇔U) was synthesized and the inhibition of PTP1B by the modified RNA at 40 nM and at 200 nM nucleic acid ligand concentrations was measured. Of these, all but three of the modifications resulted in complete loss of inhibition at these concentrations. The remaining three modifications, at positions 33, 36, and 45, resulted in moderate increases of the observed $K_i$ from approximately 35 nM to 50-60 nM. From this, it appears that the other nucleotides are either critical in the contact with the PTP1B molecule or in shaping the nucleic acid ligand into a conformation that binds with the PTP1B.

Of the 20 clones sequenced after the SELEX, in addition to the dominant sequence, C13, another sequence C9, differed from C13 in only two positions; at positions 33 and 54 C9 had a "U" whereas C13 had, respectively a "C" and a "G." As noted above, the single modification of C13 at position 33 to a U resulted in only a moderate increase in the $K_i$. The single base modification at position 54 to a "U" was also tested and also resulted in only a moderate increase in $K_i$ to 48 nM. With the two modifications (i.e. the sequence of C9 shorted to the same range as M21), the $K_i$ increased more significantly to approximately 250 nM.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of reducing the enzymatic activity of a human protein tyrosine phosphatase comprising contacting said human protein tyrosine phosphatase with an effective amount of nucleic acid ligand which exhibits binding specificity to a human protein tyrosine phosphatase, wherein the human protein tyrosine phosphatase is PTP1B, and wherein said nucleic acid ligand has a predicted secondary structure comprising a hairpin structure comprising a first region of paired nucleotides, a bulge, a second region of paired nucleotides and an end loop, wherein said bulge is located between said first and second region of paired nucleotides, and wherein said bulge is separated from said end loop by said second region of paired nucleotides, and wherein the nucleic acid ligand comprises a sequence exhibiting at least 70% sequence identity to a sequence chosen from SEQ ID NO:4, SEQ ID NO:5, SEQ ID NO:6, SEQ ID NO:7, SEQ ID NO:9 and SEQ ID NO:10.

2. The method of claim 1, wherein the nucleic acid ligand comprises a ribonucleic acid sequence.

3. The method of claim 1, wherein the nucleic acid ligand inhibits the activity of PTP1B at least 50 times more strongly than the activity of TC-PTP.

4. The method of claim 1, wherein the nucleic acid ligand inhibits the activity of PTP1B at least 100 times more strongly than the activity of TC-PTP.

5. The method of claim 1, wherein the nucleic acid ligand inhibits the activity of PTP1B at least 200 times more strongly than the activity of TC-PTP.

6. The method of claim 1, wherein the nucleic acid ligand inhibits the activity of PTP1B about 300 times more strongly than the activity of TC-PTP.

7. The method of claim 1, wherein the nucleic acid ligand comprises any of the sequences as set forth in SEQ ID NO:4, SEQ ID NO:5, SEQ ID NO:6, SEQ ID NO:7, SEQ ID NO:9 or SEQ ID NO:10.

8. A method of inhibiting the activity of protein tyrosine phosphatase 1B (PTP1B) expressed in vivo in a cell comprising introducing to the cell a vector encoding a sequence comprising the nucleic acid ligand which exhibits binding specificity to a human protein tyrosine phosphatase, wherein said nucleic acid ligand has a predicted secondary structure comprising a hairpin structure comprising a first region of paired nucleotides, a bulge, a second region of paired nucleotides and an end loop, wherein said bulge is located between said first and second region of paired nucleotides, and wherein said bulge is separated from said end loop by said second region of paired nucleotides, and wherein the nucleic acid ligand comprises a sequence exhibiting at least 70% sequence identity to a sequence chosen from SEQ ID NO:4, SEQ ID NO:5, SEQ ID NO:6, SEQ ID NO:7, SEQ ID NO:9 and SEQ ID NO:10.

9. The method of claim 1 wherein said bulge is at least 5 nucleotides long.

\* \* \* \* \*

SEQUENCE LISTING

<160> NUMBER OF SEQ ID NOS: 16

<210> SEQ ID NO 1
<211> LENGTH: 80
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(56)
<223> OTHER INFORMATION: a, c, u, g, unknown or other

<400> SEQUENCE: 1
gggaauggau ccacaucuac gaauucnnnn nnnnnnnnnn nnnnnnnnnn nnnnnnuuca    60
cugcagacuu gacgaagcuu                                                80

<210> SEQ ID NO 2
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gggaauggau ccacaucuac gaauucgug aucaauuugg caauccgcca cacgaguuca     60
cugcagacuu gacgaagcuu                                                80

<210> SEQ ID NO 3
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gggaauggau ccacaucuac gaauucugug auuaauuugg caauccgcca cacuaguuca   60
cugcagacuu gacgaagcuu                                                80

<210> SEQ ID NO 4
<211> LENGTH: 77
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gggaauggau ccacaucuac gaauucucuc gcaggcaagc uaacugagau cacuucacug   60
cagacuugac gaagcuu                                                   77

<210> SEQ ID NO 5
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gggaauucug ugaucaauuu ggcaauccgc cacacgaguu c                        41

<210> SEQ ID NO 6
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 6
gggauucugu gaucaauuug gcaauccgcc acacgagu                            38

<210> SEQ ID NO 7
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gggucuguga ucaauuuggc aauccgccac acga                                34

<210> SEQ ID NO 8
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gggugugauc aauuuggcaa uccgccacac                                     30

<210> SEQ ID NO 9
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gggugaucaa uuggcaauc cgccacac                                        28

<210> SEQ ID NO 10
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gggugaucaa uuggcaauc cgccaca                                         27

<210> SEQ ID NO 11
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gggaucaauu uggcaauccg ccac                                           24

<210> SEQ ID NO 12
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
```

-continued

```
ggguggcaau ccgcca                                                       16

<210> SEQ ID NO 13
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gggcaauccg cc                                                           12

<210> SEQ ID NO 14
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gggaauggau ccacaucuac gaauucugug aucaauuugg caauccgcca cacgaguuca       60
cugcagacuu gacgaagcuu                                                   80

<210> SEQ ID NO 15
<211> LENGTH: 3318
<212> TYPE: DNA
<213> ORGANISM: Homo sapiens

<400> SEQUENCE: 15
gtgatgcgta gttccggctg ccggttgaca tgaagaagca gcagcggcta gggcggcggt       60
agctgcaggg gtcggggatt gcagcgggcc tcggggctaa gagcgcgacg cggcctagag      120
cggcagacgc gcagtgggc cgagaaggag gcgcagcagc cgccctggcc cgtcatggag      180
atggaaaagg agttcgagca gatcgacaag tccgggagct gggcggccat ttaccaggat      240
atccgacatg aagccagtga cttcccatgt agagtggcca agcttcctaa gaacaaaaac      300
cgaaataggt acagagacgt cagtcccttt gaccatagtc ggattaaact acatcaagaa      360
gataatgact atatcaacgc tagttttgata aaaatggaag aagcccaaag gagttacatt      420
cttacccagg gcccttttgcc taacacatgc ggtcactttt gggagatggt gtgggagcag      480
aaaagcaggg gtgtcgtcat gctcaacaga gtgatggaga aggttcgtt aaaatgcgca      540 caatactggc cacaaaaaga agaaaaagag atgatctttg aagacacaaa tttgaaatta      600
acattgatct ctgaagatat caagtcatat tatacagtgc gacagctaga attggaaaac      660
cttacaaccc aagaaactcg agagatctta catttccact ataccacatg gcctgacttt      720
ggagtccctg aatcaccagc ctcattcttg aactttcttt tcaaagtccg agagtcaggg      780
tcactcagcc cggagcacgg gccgttgtg gtgcactgca gtgcaggcat cggcaggtct      840
ggaaccttct gtctggctga tacctgcctc ttgctgatgg acaagaggaa agaccctttct      900 tccgttgata tcaagaaagt gctgttagaa atgaggaagt tcggatgg gctgatccag      960 acagccgacc agctgcgctt ctcctacctg gctgtgatcg aaggtgccaa attcatcatg     1020
ggggactctt ccgtgcagga tcagtggaag gagctttccc acgaggacct ggagccccca     1080
cccgagcata tcccccccacc tccccggcca cccaaacgaa tcctggagcc acacaatggg     1140
aaatgcaggg agttcttccc aaatcaccag tgggtgaagg aagagaccca ggaggataaa     1200
gactgcccca tcaaggaaga aaaaggaagc cccttaaatg ccgcacccta cggcatcgaa     1260
```

```
agcatgagtc aagacactga agttagaagt cgggtcgtgg ggggaagtct tcgaggtgcc    1320
caggctgcct ccccagccaa aggggagccg tcactgcccg agaaggacga ggaccatgca    1380
ctgagttact ggaagccctt cctggtcaac atgtgcgtgg ctacggtcct cacgccggc    1440 gcttacctct gctacaggtt cctgttcaac agcaacacat agcctgaccc tcctccactc    1500
cacctccacc cactgtccgc ctctgcccgc agagcccacg cccgactagc aggcatgccg    1560
cggtaggtaa gggccgccgg accgcgtaga gagccgggcc ccggacggac gttggttctg    1620
cactaaaacc catcttcccc ggatgtgtgt ctcacccctc atccttttac ttttttgcccc   1680 ttccactttg agtaccaaat ccacaagcca ttttttgagg agagtgaaag agagtaccat    1740
gctggcggcg cagagggaag gggcctacac ccgtcttggg gctcgcccca cccagggctc    1800
cctcctggag catcccaggc gggcggcacg ccaacagccc ccccccttgaa tctgcaggga   1860 gcaactctcc actccatatt tatttaaaca attttttccc caaaggcatc catagtgcac    1920
tagcattttc ttgaaccaat aatgtattaa aattttttga tgtcagcctt gcatcaaggg    1980
ctttatcaaa aagtacaata ataaatcctc aggtagtact gggaatggaa ggctttgcca    2040
tgggcctgct gcgtcagacc agtactggga aggaggacgg ttgtaagcag ttgttattta    2100
gtgatattgt gggtaacgtg agaagataga acaatgctat aatatataat gaacacgtgg    2160
gtatttaata agaaacatga tgtgagatta ctttgtcccg cttattctcc tccctgttat    2220
ctgctagatc tagttctcaa tcactgctcc cccgtgtgta ttagaatgca tgtaaggtct    2280
tcttgtgtcc tgatgaaaaa tatgtgcttg aaatgagaaa ctttgatctc tgcttactaa    2340
tgtgccccat gtccaagtcc aacctgcctg tgcatgacct gatcattaca tggctgtggt    2400
tcctaagcct gttgctgaag tcattgtcgc tcagcaatag ggtgcagttt tccaggaata    2460
ggcatttgcc taattcctgg catgacactc tagtgacttc ctggtgaggc ccagcctgtc    2520
ctggtacagc agggtcttgc tgtaactcag acattccaag ggtatgggaa gccatattca    2580
cacctcacgc tctggacatg atttagggaa gcagggacac ccccgcccc ccacctttgg     2640 gatcagcctc cgccattcca agtcaacact cttcttgagc agaccgtgat ttggaagaga    2700
ggcacctgct ggaaaccaca cttcttgaaa cagcctgggt gacggtcctt taggcagcct    2760
gccgccgtct ctgtcccggt tcaccttgcc gagagaggcg cgtctgcccc accctcaaac    2820
cctgtggggc ctgatggtgc tcacgactct tcctgcaaag ggaactgaag acctccacat    2880
taagtggctt tttaacatga aaaacacggc agctgtagct cccgagctac tctcttgcca    2940
gcattttcac attttgcctt tctcgtggta gaagccagta cagagaaatt ctgtggtggg    3000
aacattcgag gtgtcaccct gcagagctat ggtgaggtgt ggataaggct taggtgccag    3060
gctgtaagca ttctgagctg ggcttgttgt ttttaagtcc tgtatatgta tgtagtagtt    3120
tgggtgtgta tatatagtag catttcaaaa tggacgtact ggtttaacct cctatccttg    3180
gagagcagct ggctctccac cttgttacac attatgttag agaggtagcg agctgctctg    3240
ctatatgcct taagccaata tttactcatc aggtcattat ttttttacaat ggccatggaa    3300 taaaccattt ttacaaaa                                                  3318
```

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

```
<400> SEQUENCE: 16

His His His His His His
1               5
```